US008415488B2

(12) United States Patent
Pugin et al.

(10) Patent No.: US 8,415,488 B2
(45) Date of Patent: *Apr. 9, 2013

(54) BIDENTATE SECONDARY PHOSPHINE OXIDE CHIRAL LIGANDS FOR USE IN ASYMMETRIC ADDITION REACTIONS

(75) Inventors: Benoît Pugin, Münchenstein (CH); Heidi Landert, Bourrignon (CH); Björn Gschwend, Zeiningen (CH); Andreas Pfaltz, Binningen (CH); Felix Spindler, Starrkirch-Wil (CH)

(73) Assignee: Solvias AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/734,726

(22) PCT Filed: Nov. 14, 2008

(86) PCT No.: PCT/EP2008/065605
§ 371 (c)(1),
(2), (4) Date: May 19, 2010

(87) PCT Pub. No.: WO2009/065783
PCT Pub. Date: May 28, 2009

(65) Prior Publication Data
US 2011/0098485 A1     Apr. 28, 2011

(30) Foreign Application Priority Data

Nov. 20, 2007  (CH) ...................................... 1788/07

(51) Int. Cl.
*C07D 333/62* (2006.01)
(52) U.S. Cl.
USPC ............................................................ 549/6
(58) Field of Classification Search ............... 549/6, 220
See application file for complete search history.

(56) References Cited

FOREIGN PATENT DOCUMENTS

| WO | 00/21663 | 4/2000 |
| WO | 2007/135179 | 11/2007 |

OTHER PUBLICATIONS

International Search Report issued Apr. 15, 2009 in International (PCT) Application No. PCT/EP2008/065605.
PCT Written Opinion issued Apr. 15, 2009 in International (PCT) Application No. PCT/EP2008/065605.
Michael Baacke et al., "Oligophosphaalkane, II Tetra- und pentakoordinierte Komplexe α,ω-PH-funktioneller Triphosphaalkane $H_{2-n}R_nP-[CH_2]_3-PR'-[CH_2]_3-PR_nH_{2-n}$", Chemische Berichte, vol. 114, No. 7, pp. 2568-2579, Jul. 1981.
Leila Boubekeur et al., "Nitrogen-assisted ortho lithiation: One-pot synthesis of new classes of bidentate and tetradentate mixed P~N Ligands", Organometallics, vol. 25, No. 12, pp. 3091-3094, 2006.
O.L. Butkova et al., "Synthesis of bonding bidentate organosilicon phosphorus ligands", Bulletin of the Academy of Sciences of the USSR, Division of Chemical Sciences, vol. 31, No. 10, pp. 2106-2108, 1982.
P. Gary Eller et al., "Syntheses of new tetrafluoroaryl derivatives of phosphorus and sulfur", Journal of Organometallic Chemistry, vol. 22, No. 3, pp. 631-636, May 1970.
George Y. Li et al., "Versatile Approaches to the Polymer-Supported Synthesis of Biodentate Phosphorus-Containing Ligands", Angewandte Chemie, International Edition, vol. 40, No. 6, pp. 1106-1109, Mar. 16, 2001.
Sibbele Hietkamp et al., "Synthese und NMR-spektroskopische Charakterisierung PH-funktioneller methylenverbrückter Diphosphane $R_2P-CH_2-PRH$ und $HRP-CH_2-PRH$", Chemische Berichte, vol. 117, pp. 3400-3413, 1984.
Xiao-bin Jiang et al., "Application of Monodentate Secondary Phosphine Oxides, a New Class of Chiral Ligands, in Ir(I)-Catalyzed Asymmetric Imine Hydrogenation", Organic Letters, vol. 5, No. 9, pp. 1503-1506, May 2003.
Xiao-bin Jiang et al., "The application of monodentate secondary phosphine oxide ligands in rhodium- and iridium-catalyzed asymmetric hydrogenation", Tetrahedron Asymmetry, vol. 15, No. 14, pp. 2223-2229, Jul. 26, 2004.
Xiaobin Jiang et al., "Monodentate secondary phospine oxides (SPO's), Synthesis and application in asymmetric catalysis", Internet Citation, [Online] XP007903156, pp. 1-173, Apr. 1972.
R.B. King et al., "Poly(tertiary phosphines and arsines). 15. Some polyphosphines with terminal dialkylamino and alkoxy groups", Journal of the American Chemical Society, vol. 99, No. 12, pp. 4001-4008, Jun. 8, 1977.
Wenjun Tang et al., "New Chiral Phosphorus Ligands for Enantioselective Hydrogenation", Chemical Reviews, vol. 103, pp. 3029-3069, 2003.
Jiang X-B: "Monodentate secondary phosphine oxides (SPO's), Synthesis and application in asymmetric catalysis", Internet Citation, [Online] XP007903156, pp. 1-173, p. 47; compound L3.11, Nov. 29, 2004, retrieved from the internet on Oct. 4, 2007: URL: http://dissertations.ub.rug.nl/FILES/faculties/science/2004/x.jiang/thesis.pdf.

*Primary Examiner* — Taofiq A Solola
(74) *Attorney, Agent, or Firm* — Wenderoth, Lind & Ponack, L.L.P.

(57) ABSTRACT

Compounds of the formula I, in the form of mixtures comprising predominantly one enantiomer or in the form of pure enantiomers, secondary phosphine-Q-P*(=O)HR₁ (I) in which secondary phosphine is a C-bonded, secondary phosphine group —P(R)₂; in which R is in each case independently hydrocarbon radicals or heterohydrocarbon radicals; Q is a bivalent, achiral, aromatic base skeleton, a bivalent, achiral ferrocene base skeleton, an optionally substituted bivalent cycloalkane or heterocycloalkane skeleton, or a C1-C4-alkylene skeleton, and in which base skeletons a secondary phosphine group is bonded directly to a carbon atom, or, in the case of cyclic base skeletons, directly to a carbon atom or via a $C_1$-$C_4$-alkylene group, and in which base skeletons a P-chiral group —P*(O)HR₁ is bonded to a carbon atom such that the phosphorus atoms are linked via 1 to 7 atoms of a carbon chain optionally interrupted by heteroatoms from the group of O, S, N, Fe or Si; P* is a chiral phosphorus atom; and R₁ is a hydrocarbon radical, a C-bonded heterohydrocarbon radical or a ferrocenyl radical, with the proviso that R₁ is an achiral ferrocenyl radical when Q is an achiral ferrocenyl base skeleton. Metal complexes of these ligands in a molar ratio of ligand to metal of about 1.3:1 to 0.9:1 are homogeneous catalysts for asymmetric addition reactions, particularly hydrogenations.

16 Claims, No Drawings

BIDENTATE SECONDARY PHOSPHINE OXIDE CHIRAL LIGANDS FOR USE IN ASYMMETRIC ADDITION REACTIONS

The present invention relates to optically enriched or optically pure chiral ligands with a bivalent, achiral, aromatic base skeleton, a bivalent, achiral ferrocene base skeleton, an optionally substituted bivalent cycloalkane or heterocycloalkane skeleton, or a $C_1$-$C_4$-alkylene skeleton, in which base skeletons a secondary phosphine group is bonded directly to a carbon atom, or, in the case of cyclic base skeletons, directly to a carbon atom or via a $C_1$-$C_4$-alkylene group, and in which base skeletons an optically enriched or optically pure P-chiral group —P*(O)HR$_1$ is bonded to a carbon atom such that the phosphorus atoms are linked via 1 to 7 atoms of a carbon chain optionally interrupted by heteroatoms from the group of O, S, N, Fe or Si; to metal complexes of these bidentate ligands with transition metals; and to the use of the metal complexes in asymmetric syntheses, particularly in hydrogenations with hydrogen of prochiral organic compounds which contain at least one carbon/carbon or carbon/heteroatom double bond.

Metal complexes with chiral ligands have been found to be valuable catalysts in asymmetric syntheses. Practical benefit is possessed by those metal complexes with which, as well as sufficient catalytic activity, a high stereoselectivity can also be achieved. Without these two properties, there can be no implementation in industrial processes for economic reasons.

It is to date still impossible to predict which metal complexes with which ligands under which reaction conditions with which unsaturated substrates will give rise to practically usable hydrogenation results with regard to the catalytic activity and stereoselectivity. A multitude of different bidentate ligands has therefore been provided, which may contain chelating groups with oxygen, sulphur, nitrogen and/or phosphorus atoms (see for example W. Teng, X. Zhang, Chem. Rev. 2003, 103, 3029-3069). Among these bidentate ligands, P^N and P^P ligands have frequently been found to be useful, particularly when the chelating groups are bonded to aromatics with atropisomerism (bisarenes and bisheteroarenes) or planar isomerism (metallocenes).

P. G. Gary et al. describe, in J. of Organomet. Chem. (1972) 22(3), 631-636, the synthesis of racemic 1-diphenylphosphine-2-pentafluorophenylphosphine oxide-tetrafluorophenylene, no mention being made of its catalytic properties.

WO 00/21663 describes diphosphines with RHP(=O) groups bonded via carbon atoms to a base skeleton and secondary phosphine groups —PR$_a$R$_b$, which are proposed as ligands for transition metals to form catalytic compounds. WO 00/21663 does not contain any indications to stereoselective syntheses, and only the preparation of achiral coumarin is described. Therefore, no optically enriched or pure, chiral ligands for stereoselective catalysts are mentioned either.

Recently, a bidentate ligand of the formula (A) has been described [see thesis by Xiaobin Jiang with Prof. J. G. de Vries and Prof. B. L. Feringa, University of Groningen 29 Nov. 2004 (ISBN: 90-367-2144X), which is not mentioned in later publications by Xiaobin Jiang et al. in Org. Lett., 5 (2003) 1503-6 and Tetrahedron: Asymmetry, 15 (2004) 2223-9]: this ligand was prepared as a racemate and optically resolved by HPLC with a chiral column.

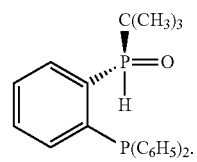
(A)

The enantiomeric ligand of the formula A has been used in an Rh complex in a ligand/metal molar ratio of 2/1 for the asymmetric hydrogenation of 1-phenylvinyl-dimethylcarbamate (thesis of Xiaobin Jiang, chapter 6, table 6.5, page 159), with disappointing results, namely low stereoselectivities and very low catalyst activities (TOF<1 h$^{-1}$), and the asymmetric hydrogenation of N-benzyl-N-[1-phenylethylidene]amine (chapter 5, pages 120 and 125) with an Ir complex, with only very low stereoselectivities and catalyst activities.

In contrast to these results, it has now been found that, surprisingly, metal complexes of ligand A and other bidentate ligands with a stereogenic, P-chiral centre of the formula —P(O)HR$_1$ can achieve high catalyst activities in the hydrogenation of unsaturated, prochiral compounds containing a carbon or carbon-heteroatom double bond when the ligand/metal molar ratio is from 1.3/1 to 0.9/1. It has also been found that, surprisingly, diphosphines with a P(O)HR$_1$ group, in enantioselective hydrogenations of substrates other than 1-phenylvinyl-dimethylcarbamate and N-benzyl-N-[1-phenylethylidene]amine with transition metal complexes, are notable for very high catalyst activities and additionally often achieve good to very good stereoselectivities. Finally it was also surprisingly found that optically enriched or pure mixed phosphine-SPO ligands including that of formula (A) can be prepared by stereoselective synthesis without the need of separation by HPLC on a chiral column.

The invention is as defined in the claims.

The invention firstly provides compounds of the formula I, in the form of mixtures comprising predominantly one enantiomer or in the form of pure enantiomers,

secondary phosphine-Q-P*(=O)HR$_1$      (I)

in which secondary phosphine is a C-bonded secondary phosphine group —P(R)$_2$; in which R is in each case independently hydrocarbon radicals or heterohydrocarbon radicals;

Q is a bivalent, achiral, aromatic base skeleton, a bivalent, achiral ferrocene base skeleton, an optionally substituted bivalent cycloalkane or heterocycloalkane skeleton, or a $C_1$-$C_4$-alkylene skeleton, and in which base skeletons a secondary phosphine group is bonded directly to a carbon atom, or, in the case of cyclic base skeletons, directly to a carbon atom or via a $C_1$-$C_4$-alkylene group, and in which base skeletons a P-chiral group —P*(=O)HR$_1$ is bonded directly to a carbon atom, or, in the case of cyclic base skeletons, directly to a carbon atom or via a $C_1$-$C_4$-alkylene group to a carbon atom such that the phosphorus atoms of the secondary phosphine group and the P-chiral group —P*(=O)HR$_1$ are linked via 1 to 7 atoms of a carbon chain optionally interrupted by heteroatoms from the group of O, S, N, Fe or Si;

P* is a chiral phosphorus atom; and

R$_1$ is a hydrocarbon radical, a C-bonded heterohydrocarbon radical or a ferrocenyl radical, with the proviso that R$_1$ is an achiral ferrocenyl radical when Q is an achiral ferrocenyl base skeleton, excluding the compound of the formula A

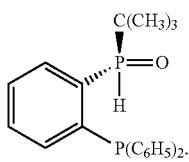

(A)

By way of explanation, it should be noted that the compounds of the formula (I) and formula A also include the tautomeric forms in which the —P*(=O)HR$_1$ group is represented as the hydroxyl form —P*(OH)R$_1$. In the two tautomeric forms, the phosphorus atom is asymmetric and chiral.

In the context of the invention, "predominantly enantiomeric" means that, in mixtures, one enantiomer is present in an amount of at least 85% by weight, preferably at least 90% by weight and more preferably at least 95% by weight. The compounds of the formula (I) are thus optically enriched or optically pure chiral ligands.

The carbon chain via which the phosphorus atoms are linked may be part of a cyclic skeleton only, or be part of a cyclic skeleton and unsubstituted or substituted alkylene groups bonded thereto. The carbon chain via which the phosphorus atoms are linked contains preferably 1 to 5 carbon atoms or 1 to 4 carbon atoms and a heteroatom to form the —C—C—He—C—C sequence where He is O, S and N(C$_1$-C$_6$-alkyl). In a 1,1'-ferrocenediyl, the carbon chain interrupted by Fe, in a formal sense, has the —C—Fe—C— sequence. The carbon chain may be part of a ring, part of fused rings or part of linked rings (biphenylenes). In a particularly preferred embodiment, the phosphorus atoms are linked via a carbon chain having 1 to 4 carbon atoms. More preferably, the phosphorus atoms are linked via a carbon chain having 1 to 4 carbon atoms or via the —C—Fe—C— group.

The secondary phosphine group and the P(O)HR$_1$ group may be bonded to a cyclic base skeleton either directly or via a bivalent C$_1$-C$_4$-carbon group. It is thus an alkylene group which is unsubstituted or substituted by C$_1$-C$_6$-alkyl (for example methyl, ethyl, n-propyl or n-butyl), C$_1$-C$_6$-alkoxy (for example methoxy, ethoxy, n-propoxy or n-butoxy), benzyl, benzyloxy, phenyl, phenyloxy, cyclopentyl, cyclopentyloxy, cyclohexyl, cyclohexyloxy, di(C$_1$-C$_4$-alkyl)amino (for example dimethylamino and diethylamino), piperidinyl or morpholinyl and has 1 to 4 and preferably 1 or 2 carbon atoms. The alkylene group is preferably methylene or ethylene or corresponds to the formula —CHR$_8$— in which R$_8$ is C$_1$-C$_4$-alkyl, cyclohexyl or phenyl. The substitution of the bivalent C$_1$-C$_4$-alkylene group may lead to further asymmetric carbon atoms, such that the compounds of the formula (I) then have at least one further chiral centre. The C$_1$-C$_4$-alkylene group is preferably methylene, ethylene or C$_2$-C$_6$-alkylidene. Examples of alkylidene are ethylidene, 1,1-propylidene and 1,1-butylidene.

In a preferred embodiment, the secondary phosphine group and the *P(O)HR$_1$ group are bonded to the base skeleton Q directly, via ethylene or a radical of the formula —CHR$_8$ in which R$_8$ is hydrogen, methyl or ethyl. The secondary phosphine group and the P(O)HR$_1$ group are more preferably bonded directly to cyclic radicals.

The bivalent, aromatic base skeleton Q does not contain an axial chiral centre or planar chiral centre. Substitutions on the aromatic base skeleton Q therefore must not lead to a bivalent base skeleton with an axial chiral centre or a planar chiral centre.

The Q group may be unsubstituted or, for example, mono- to hexasubstituted, preferably mono- to tetrasubstituted and more preferably mono- to disubstituted by substituents R$_x$ such as halogen, or a hydrocarbon radical which is inert under reaction conditions and is bonded via a carbon atom, oxygen atom, sulphur atom, nitrogen atom or silicon atom, where hydrocarbon radicals in the substituents R$_x$ may themselves be substituted. When the Q group is a cyclic radical, these radicals may also be provided with ring-forming substituents, for example C$_2$-C$_4$-alkylene, C$_2$-C$_4$-alkenylene, C$_4$-C$_8$-alkadienylene, C$_1$-C$_2$-alkylenediamino or C$_1$-C$_2$-alkylenedioxy. When at least two substituents in the Q group are bonded, they may be the same or different.

The optionally substituted substituent R$_x$ may, for example, be C$_1$-C$_{12}$-alkyl, preferably C$_1$-C$_8$-alkyl and more preferably C$_1$-C$_4$-alkyl. Examples are methyl, ethyl, n- or i-propyl, n-, i- or t-butyl, pentyl, hexyl, octyl, decyl, undecyl and dodecyl.

The optionally substituted substituent R$_x$ may, for example, be C$_5$-C$_8$-cycloalkyl, preferably C$_5$-C$_6$-cycloalkyl. Examples are cyclopentyl, cyclohexyl and cyclooctyl.

The optionally substituted substituent R$_x$ may, for example, be C$_5$-C$_8$-cycloalkylalkyl, preferably C$_5$-C$_6$-cycloalkylalkyl having, for example, 1 to 4 carbon atoms in the alkyl. Examples are cyclopentylmethyl, cyclohexylmethyl or -ethyl and cyclooctylmethyl.

The optionally substituted substituent R$_x$ may, for example, be C$_6$-C$_{18}$-aryl and preferably C$_6$-C$_{10}$-aryl. Examples are phenyl or naphthyl.

The optionally substituted substituent R$_x$ may, for example, be C$_7$-C$_{12}$-aralkyl, for example benzyl or 1-phenyleth-2-yl.

The optionally substituted substituent R$_x$ may, for example, be tri(C$_1$-C$_4$-alkyl)Si or triphenylsilyl. Examples of trialkylsilyl are trimethyl-, triethyl-, tri-n-propyl-, tri-n-butyl- and dimethyl-t-butylsilyl.

The substituent R$_x$ may, for example, be halogen. Examples are F and Cl.

The optionally substituted substituent R$_x$ may, for example, be an amino radical, an alkoxy radical or thio radical of the formulae —N(R$_{05}$)$_2$, —OR$_{05}$ and —SR$_{05}$, in which R$_{05}$ is C$_1$-C$_{12}$-alkyl, preferably C$_1$-C$_8$-alkyl and more preferably C$_1$-C$_4$-alkyl; C$_5$-C$_8$-cycloalkyl, preferably C$_5$-C$_6$-cycloalkyl; C$_6$-C$_{18}$-aryl and preferably C$_6$-C$_{10}$-aryl; or C$_7$-C$_{12}$-aralkyl. Examples of these hydrocarbon radicals have already been mentioned above for the substituents.

The hydrocarbon radicals of the substituents R$_x$ may in turn be mono- or polysubstituted, for example mono- to trisubstituted, preferably mono- or disubstituted, for example by halogen (F or Cl, particularly F), —NR$_{001}$R$_{002}$, C$_1$-C$_4$-alkyl, C$_1$-C$_4$-alkoxy, C$_1$-C$_4$-alkylthio, C$_5$-C$_6$-cycloalkyl, phenyl, benzyl, phenoxy or benzyloxy, where R$_{001}$ and R$_{002}$ are each independently C$_1$-C$_4$-alkyl, cyclopentyl, cyclohexyl, phenyl, benzyl, or R$_{001}$ and R$_{002}$ together are tetramethylene, pentamethylene or 3-oxapentane-1,5-diyl. The hydrocarbon radicals of the substituents R$_x$ are preferably unsubstituted.

Q is preferably unsubstituted or substituted by CF$_3$, F, Cl, C$_1$-C$_4$-alkyl, C$_1$-C$_4$-alkoxy, C$_1$-C$_4$-alkylthio, (C$_1$-C$_4$-alkyl)$_2$N or (C$_1$-C$_4$-alkyl)$_3$Si.

In a preferred embodiment, Q is
(a) a bivalent arene or heteroarene,
(b) 1,1'-biaryl-2,2'-diyl, 1,1'-biheteroaryl-2,2'-diyl and 1,1'-arylheteroaryl-2,2'-diyl, each optionally attached via a bridge group,
(c) 1,1'-ferrocenylene;

(d) $C_4$-$C_8$-cycloalkylene-1,2- or 1,3-diyl or $C_3$-$C_7$-heterocycloalkylene-1,2- or 1,3-diyl with N, NH or $N(C_1$-$C_4$-alkyl), O or S heteroatoms, or (e) linear $C_1$-$C_4$-alkylene, where these radicals are unsubstituted or substituted, for example by halogen (F, Cl or Br), $CF_3$, $(C_1$-$C_4$-alkyl$)_2$N, $C_1$-$C_4$-alkyl, $C_1$-$C_4$-alkoxy, or a ring-forming alkylenedioxy group.

A bivalent, aromatic base skeleton may be a 1,2-arene or 1,2-heteroarene. This bivalent, aromatic base skeleton Q may be $C_6$-$C_{22}$-arylene or $C_2$-$C_{20}$-heteroarylene having one or more heteroatoms or heteroatomic groups selected from the group of —O—, —S—, —$NR_{06}$— and —N═, where $R_{06}$ is H, $C_1$-$C_8$-alkyl, $C_3$-$C_8$-cycloalkyl, $C_3$-$C_8$-cycloalkyl-$C_1$-$C_4$-alkyl, $C_6$-$C_{10}$-aryl, $C_6$-$C_{10}$-aryl-$C_1$-$C_4$-alkyl or a protecting group. Protecting groups are, for example, acyl, for example $C_1$-$C_8$-acyl or $C_1$-$C_8$-haloacyl derived from carbonic acids or sulphonic acids, or N,N-di-$C_1$-$C_4$-alkylaminocarbonyl, for example dimethylaminocarbonyl. In the heteroarylene, at least 2 ring carbon atoms are bonded to one another. Heteroarylene contains preferably 5 or 6 ring atoms and preferably 1 to 3, more preferably 1 or 2 heteroatoms in the ring. Arylene and heteroarylene may be aromatic or aromatic-aliphatic, fused ring systems. Heteroarylene may contain a plurality of heteroatoms in the same or different rings of fused ring systems.

In a preferred configuration, the bivalent, aromatic base skeleton Q is $C_6$-$C_{14}$-arylene and more preferably $C_6$-$C_{10}$-arylene. Examples of arylene are 1,2-phenylene, 1,2-, 2,3- or 1,8-naphthylene, 1,2-, 2,3-, 4,5-, 5,6- or 9,10-phenanthrenylene, 1,2-, 2,3-anthracenylene, 1,2-, 2,3-naphthacenylene, 1,2- or 2,3-fluorenylene and 1,2- or 3,4-perylenylene. Particularly preferred arylene radicals are naphthylene and phenylene.

In another preferred configuration, the bivalent, aromatic base skeleton Q is $C_3$-$C_{14}$- and more preferably $C_4$-$C_{10}$-heteroarylene having one to three heteroatoms or heteroatomic groups selected from the group of —O—, —S—, —$NR_{06}$— or —N═, where $R_{06}$ is H, $C_1$-$C_4$-alkyl or a protecting group. Examples of heteroarylene are 1,2- or 2,3-furanylene, 1,2- or 2,3-thiophenylene, 1,2- or 2,3-pyrrolylene, 4,5-thiazolylene, 4,5-isoxazolylene, 3,4- or 4,5-pyrazolylene, 4,5-imidazolylene, 2,3- or 5,6-benzofuranylene, 2,3- or 5,6-benzthiophenylene, 2,3- or 5,6-indolylene, 2,3- or 3,4-pyridinylene, 4,5- or 5,5-pyrimidinylene, 3,4-pyridazinylene, 2,3-pyrazinylene, 2,3- or 5,6-quinolinylene, 3,4-isoquinolinylene and 2,3-quinoxalinylene. Preferred heteroarylenes are furanylene, thiophenylene, benzofuranylene and benzthiophenylene.

A bivalent, aromatic base skeleton may be a 2,2'-biphenylene. These biphenylenes are aryl, heteroaryl or aryl and heteroaryl bonded in the 1,1'-positions, optionally via a bridging group $X_1$. Aryl and heteroaryl may also be fused ring systems. Aryl may be $C_6$-$C_{12}$-aryl (preferably naphthyl and more preferably phenyl), and heteroaryl may be $C_3$-$C_{11}$-heteroaryl having one or more heteroatoms or heteroatomic groups selected from the group of —O—, —S—, —$NR_{06}$— and —N═, where $R_{06}$ is H, $C_1$-$C_8$-alkyl, $C_3$-$C_8$-cycloalkyl, $C_3$-$C_8$-cycloalkyl-$C_1$-$C_4$-alkyl, $C_6$-$C_{10}$-aryl, $C_6$-$C_{10}$-aryl-$C_1$-$C_4$-alkyl or a protecting group. Protecting groups are, for example, acyl, for example $C_1$-$C_8$-acyl or $C_1$-$C_8$-haloacyl derived from carboxylic acids or sulphonic acids, or N,N-di-$C_1$-$C_4$-alkylaminocarbonyl, for example dimethylaminocarbonyl. The heteroaryl is preferably monocyclic, contains preferably 5 or 6 ring atoms and preferably 1 to 3, more preferably 1 or 2 heteroatoms in the ring. Examples of preferred heteroaryl are thiophenyl, furanyl, N-methylpyrrolinyl, benzothiophenyl, benzofuranyl and indolyl. The bridging group $X_1$ may be selected from —O—, —S—, —$NR_{07}$—, $C_1$-$C_2$-alkylene, $C_2$-$C_{18}$-alkylidene, $C_3$-$C_6$-cycloalkyl-1,2-ene or $C_3$-$C_6$-cycloalkylidene, —CH(O—$C_1$-$C_4$-alkyl)- and —Si$(R_{07})_2$—, where $R_{07}$ is $C_1$-$C_{12}$-alkyl, $C_5$- or $C_6$-cycloalkyl, $C_5$- or $C_6$-cycloalkylmethyl or -ethyl, phenyl, benzyl or 1-phenyleth-2-yl.

In a preferred embodiment, the 2,2'-biphenylene is phenyl or naphthdiyl bonded directly or via a bridging group $X_1$, where $X_1$ is —$CH_2$—, —$(CH_2)_2$—, $C_2$-$C_8$-alkylidene, cyclopentylidene, cyclohexylidene, —O—, —S—, —$NR_{07}$— or —Si$(R_{07})_2$—, and $R_{07}$ is $C_1$-$C_4$-alkyl, and where the two phenyls in the two other ortho positions may be bonded to methylene, ethylene, $C_2$-$C_8$-alkylidene, —O— or —$(C_1$-$C_4$-alkyl)N—, to form a tricyclic system.

A bivalent, aromatic base skeleton may be a 1,1'-ferrocenylene of the formula

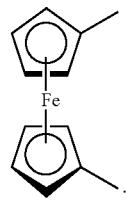

A bivalent base skeleton may be a 1,2- or 1,3-$C_3$-$C_{12}$-, preferably $C_4$ to $C_{10}$-cycloalkylene. They may be mono- or polycyclic radicals (fused ring systems having, for example, 2 to 4 rings). Some examples are 1,2-cyclopropylene, 1,2- or 1,3-cyclobutylene, 1,2- or 1,3-cyclopentylene, 1,2- or 1,3-cyclohexylene, 1,2- or 1,3-cycloheptylene, 1,2- or 1,3-cyclooctylene, 1,2- or 1,3-cyclononylene, 1,2- or 1,3-cyclodecylene, 1,2- or 1,3-cyclododecylene, [2,2,1]-bicycloheptane-1,2-diyl, [2,2,2]-bicyclooctane-2,3-diyl and tetralin-3,4-diyl.

A bivalent base skeleton may be a 1,2- or -1,3-$C_2$-$C_{11}$—, preferably $C_3$-$C_9$-heterocycloalkylene, in which at least 2 linked carbon atoms are present in the ring. The heteroatoms may be selected from the group of —O—, —S—, —NH—, —N═ and —N(C1-C4-alkyl)-. They may be mono- or polycyclic radicals (fused ring systems having, for example, 2 to 4 rings). Some examples are pyrrolidine-2,3- or -3,4-diyl, tetrahydrofuran-2,3- or -3,4-diyl, tetrahydrothiophene-2,3- or -3,4-diyl, piperidine-2,3- or -3,4-diyl and tetrahydropyran-2,3- or -3,4-diyl.

A bivalent base skeleton may be an unsubstituted or $C_1$-$C_4$-alkyl-substituted $C_1$-$C_4$-alkylene. Preference is given to unsubstituted methylene and ethylene. Some examples are methylene, ethylene, 1,2- or 1,3-propylene, 1,2-, 1,3- or 1,4-butylene, ethylidene, 1,1- or 2,2-propylidene, and 1,1- or 2,2-butylidene.

The hydrocarbon radicals and heterohydrocarbon radicals as substituents in the secondary phosphine group may be unsubstituted or substituted and contain heteroatoms selected from the group of O, S, —N═ and N($C_1$-$C_4$-alkyl). They may contain 1 to 30, preferably 1 to 20, and more preferably 1 to 12 carbon atoms. The hydrocarbon radical or heterohydrocarbon radical may be selected from the group of linear or branched $C_1$-$C_{18}$-alkyl; unsubstituted or $C_1$-$C_6$-alkyl- or $C_1$-$C_6$-alkoxy-substituted $C_5$-$C_{12}$-cycloalkyl or $C_5$-$C_{12}$-cycloalkyl-$CH_2$—; phenyl, naphthyl, furyl or benzyl; or halogen-, $C_1$-$C_6$-alkyl-, trifluoromethyl-, $C_1$-$C_6$-alkoxy-, trifluoromethoxy-, $(C_6H_5)_3$Si—, $(C_1$-$C_{12}$-alkyl$)_3$Si—, or secondary amino-substituted phenyl, naphthyl, furyl or benzyl.

Examples of phosphorus substituents as alkyl which preferably contains 1 to 6 carbon atoms are methyl, ethyl, n-propyl, i-propyl, n-butyl, i-butyl, t-butyl, and the isomers of pentyl and hexyl. Examples of phosphorus substituents as optionally alkyl-substituted cycloalkyl are cyclopentyl, cyclohexyl, methyl- and ethylcyclohexyl, and dimethylcyclohexyl. Examples of phosphorus substituents as alkyl- and alkoxy-substituted phenyl and benzyl are methylphenyl, dimethylphenyl, trimethylphenyl, ethylphenyl, methylbenzyl, methoxyphenyl, dimethoxyphenyl, trimethoxyphenyl, trifluoromethylphenyl, bis(trifluoromethyl)phenyl, tris(trifluoromethyl)phenyl, trifluoromethoxyphenyl, bis(tri-fluoromethoxy)phenyl, fluoro- and chlorophenyl and 3,5-dimethyl-4-methoxyphenyl.

Preferred secondary phosphine groups are those which contain radicals selected from the group of $C_1$-$C_6$-alkyl, unsubstituted or mono- to tri-$C_1$-$C_4$-alkyl- or —$C_1$-$C_4$-alkoxy-substituted cyclopentyl, cyclohexyl, norbornyl or adamantyl, benzyl and particularly phenyl which is unsubstituted or substituted by 1 to 3 $C_1$-$C_4$-alkyl, $C_1$-$C_4$-alkoxy, $C_1$-$C_4$-fluoroalkyl or $C_1$-$C_4$-fluoroalkoxy, F and Cl.

The secondary phosphine group corresponds preferably to the formula —$PR_2R_3$ in which $R_2$ and $R_3$ are each independently a hydrocarbon radical or an O-atom(s) containing heterohydrocarbon radical which has 1 to 18 carbon atoms and is unsubstituted or substituted by $C_1$-$C_6$-alkyl, methyl, $C_1$-$C_6$-alkoxy, trifluoromethoxy, ($C_1$-$C_4$-alkyl)$_2$amino, ($C_6H_5$)$_3$Si, ($C_1$-$C_{12}$-alkyl)$_3$Si, halogen.

Preferably, $R_2$ and $R_3$ are radicals selected from the group of linear and branched $C_1$-$C_6$-alkyl, unsubstituted or mono- to tri-$C_1$-$C_4$-alkyl- or —$C_1$-$C_4$-alkoxy-substituted cyclopentyl or cyclohexyl, norbornyl, adamantyl, furyl, unsubstituted or mono- to tri-$C_1$-$C_4$-alkyl- or —$C_1$-$C_4$-alkoxy-substituted benzyl, and especially unsubstituted or mono- to tri-F—, —Cl—, —$C_1$-$C_4$-alkyl-, —$C_1$-$C_4$-alkoxy-, —$C_1$-$C_4$-fluoroalkyl- or —$C_1$-$C_4$-fluoroalkoxy-substituted phenyl.

More preferably, $R_2$ and $R_3$ are radicals selected from the group of $C_1$-$C_6$-alkyl, cyclopentyl, cyclohexyl, furyl, and unsubstituted or mono- to tri-F—, —Cl—, —$C_1$-$C_4$-alkyl-, —$C_1$-$C_4$-alkoxy- and/or —$C_1$-$C_4$-fluoroalkyl-substituted phenyl.

When $R_2$ and $R_3$ in the —$PR_2R_3$ group are different, the phosphorus atom of the secondary phosphine group has a chiral centre.

The secondary phosphine group may be cyclic secondary phosphino, for example those of the formulae

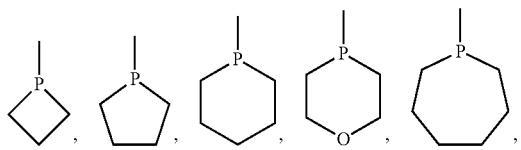

which are unsubstituted or mono- or polysubstituted by $C_1$-$C_8$-alkyl, $C_4$-$C_8$-cycloalkyl, $C_1$-$C_6$-alkoxy, $C_1$-$C_4$-alkoxy-$C_1$-$C_4$-alkyl, phenyl, $C_1$-$C_4$-alkyl- or $C_1$-$C_4$-alkoxyphenyl, benzyl, $C_1$-$C_4$-alkyl- or $C_1$-$C_4$-alkoxybenzyl, benzyloxy, $C_1$-$C_4$-alkyl- or $C_1$-$C_4$-alkoxybenzyloxy, or $C_1$-$C_4$-alkylidenedioxy.

The substituents may be bonded in one or both a positions to the phosphorus atom, in order to introduce chiral carbon atoms. The substituents in one or both α positions are preferably $C_1$-$C_4$-alkyl or benzyl, for example methyl, ethyl, n- or i-propyl, benzyl or —$CH_2$—O—$C_1$-$C_4$-alkyl or —$CH_2$—O—$C_6$-$C_{10}$-aryl.

Substituents in the β,γ positions may, for example, be $C_1$-$C_4$-alkyl, $C_1$-$C_4$-alkoxy, benzyloxy, or —O—$CH_2$—O—, —O—$CH(C_1$-$C_4$-alkyl)—O—, and —O—$C(C_1$-$C_4$-alkyl)$_2$—O—. A few examples are methyl, ethyl, methoxy, ethoxy, —O—CH(methyl)—O—, and —O—C(methyl)$_2$—O—.

According to the type of substitution and number of substituents, cyclic phosphine radicals may be C-chiral, P-chiral or C- and P-chiral.

An aliphatic 5- or 6-membered ring or benzene may be fused to two adjacent carbon atoms in the radicals of the above formulae.

The cyclic secondary phosphino may, for example, correspond to the formulae (only one of the possible enantiomers specified)

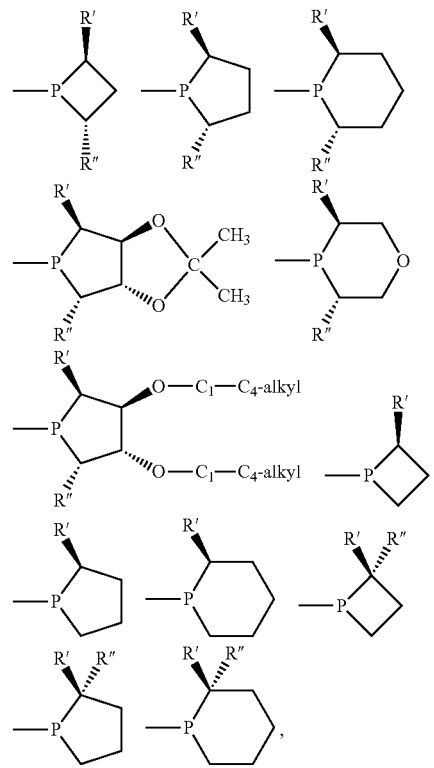

in which the R' and R" radicals are each $C_1$-$C_4$-alkyl, for example methyl, ethyl, n- or i-propyl, benzyl, or —$CH_2$—O—$C_1$-$C_4$-alkyl or —$CH_2$—O—$C_6$-$C_{10}$-aryl, and R' and R" are identical or different from one another.

In the compounds of the formula I, secondary phosphine is preferably a noncyclic secondary phosphine selected from the group of —P($C_1$-$C_6$-alkyl)$_2$, —P($C_5$-$C_8$-cycloalkyl)$_2$, —P($C_7$-$C_8$-bicycloalkyl)$_2$, —P(o-furyl)$_2$, —P($C_6H_5$)$_2$, —P[2-($C_1$-$C_6$-alkyl)$C_6H_4$]$_2$, —P[3-($C_1$-$C_6$-alkyl)$C_6H_4$]$_2$, —P[4-($C_1$-$C_6$-alkyl)$C_6H_4$]$_2$, —P[2-($C_1$-$C_6$-alkoxy)$C_6H_4$]$_2$, —P[3-($C_1$-$C_6$-alkoxy)$C_6H_4$]$_2$, —P[4-($C_1$-$C_6$-alkoxy)$C_6H_4$]$_2$, —P[2-(trifluoromethyl)$C_6H_4$]$_2$, —P[3-(trifluoromethyl)$C_6H_4$]$_2$, —P[4-(trifluoromethyl)$C_6H_4$]$_2$, —P[3,5-bis(trifluoromethyl)$C_6H_3$]$_2$, —P[3,5-bis($C_1$-$C_6$-alkyl)$_2C_6H_3$]$_2$, —P[3,5-bis($C_1$-$C_6$-alkoxy)$_2C_6H_3$]$_2$ and —P[3,5-bis($C_1$-$C_6$-alkyl)$_2$-4-($C_1$-$C_6$-alkoxy)$C_6H_2$]$_2$, or a cyclic phosphine selected from the group of

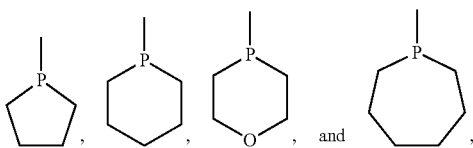

which are unsubstituted or mono- or polysubstituted by $C_1$-$C_4$-alkyl, $C_1$-$C_4$-alkoxy, $C_1$-$C_4$-alkoxy-$C_1$-$C_2$-alkyl, phenyl, benzyl, benzyloxy or $C_1$-$C_4$-alkylidenedioxy.

Some specific examples are —P(CH$_3$)$_2$, —P(i-C$_3$H$_7$)$_2$, —P(n-C$_4$H$_9$)$_2$, —P(i-C$_4$H$_9$)$_2$, —P(t-C$_4$H$_9$)$_2$, —P(C$_5$H$_9$), —P(C$_6$H$_{11}$)$_2$, —P(norbornyl)$_2$, —P(o-furyl)$_2$, —P(C$_6$H$_5$)$_2$, P[2-(methyl)C$_6$H$_4$]$_2$, P[3-(methyl)C$_6$H$_4$]$_2$, —P[4-(methyl) C$_6$H$_4$]$_2$, —P[2-(methoxy)C$_6$H$_4$]$_2$, —P[3-(methoxy)C$_6$H$_4$]$_2$, —P[4-(methoxy)C$_6$H$_4$]$_2$, —P[3-(trifluoromethyl)C$_6$H$_4$]$_2$, —P[4-(trifluoromethyl)C$_6$H$_4$]$_2$, —P[3,5-bis(trifluoromethyl)C$_6$H$_3$]$_2$, —P[3,5-bis(methyl)$_2$C$_6$H$_3$]$_2$, —P[3,5-bis(methoxy)$_2$C$_6$H$_3$]$_2$ and —P[3,5-bis(methyl)$_2$-4-(methoxy)C$_6$H$_2$]$_2$, and those of the formulae

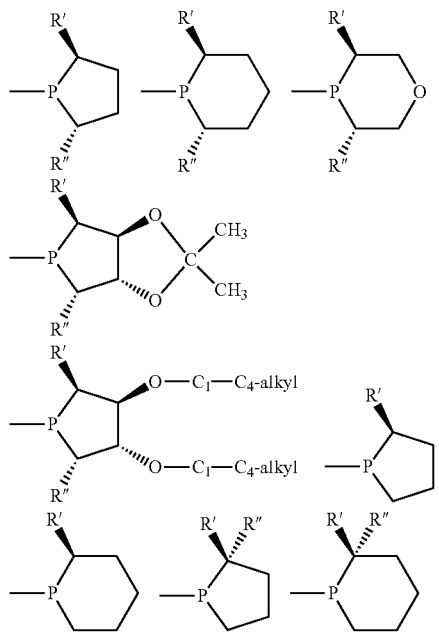

in which

R' is methyl, ethyl, methoxy, ethoxy, phenoxy, benzyloxy, methoxymethyl, ethoxymethyl or benzyloxymethyl, and R" is independently as defined for R', and is different from R'.

When $R_1$ is a hydrocarbon radical or a heterohydrocarbon radical, these radicals independently have the same definitions and preferences as the above-defined substituents in the secondary phosphine group or $R_2$ in the —PR$_2$R$_3$ group for noncyclic phosphine. $R_1$ may, for example, be a hydrocarbon radical or heteroatom radical selected from the group of linear or branched $C_1$-$C_{18}$-alkyl; unsubstituted or $C_1$-$C_6$-alkyl- or $C_1$-$C_6$-alkoxy-substituted $C_5$-$C_{12}$-cycloalkyl or $C_5$-$C_{12}$-cycloalkyl-CH$_2$—; phenyl, naphthyl, anthryl, furyl or benzyl; or halogen-, $C_1$-$C_6$-alkyl-, trifluoromethyl-, $C_1$-$C_6$-alkoxy-, trifluoromethoxy-, (C$_6$H$_5$)$_3$Si—, (C$_1$-$C_{12}$-alkyl)$_3$Si—, or secondary amino-substituted phenyl, naphthyl, anthryl, furyl or benzyl, or $R_1$ is an unsubstituted or mono- or polysubstituted ferrocenyl radical. $R_1$ may preferably be $C_1$-$C_8$-alkyl and more preferably $C_3$-$C_8$-alkyl, cyclopentyl or cyclohexyl which are unsubstituted or substituted by 1 to 3 $C_1$-$C_4$-alkyl or $C_1$-$C_4$-alkoxy, benzyl and phenyl which are unsubstituted or substituted by 1 to 3 $C_1$-$C_4$-alkyl, $C_1$-$C_4$-alkoxy, $C_1$-$C_4$-fluoroalkyl or $C_1$-$C_4$-fluoroalkoxy, F and Cl. Among the $C_3$-$C_8$-alkyl groups, preference is given to those which are α-branched. $R_1$ may also be polycyclic radicals having 2 to 4 rings, for example [2,2,1]-bicycloheptanyl or adamantyl.

When Q is 1,1'-ferrocenylene, $R_1$ is an unsubstituted ferrocenyl radical.

When $R_1$ is a ferrocenyl radical and Q is 1,2-arene, 1,2-heteroarene or a 2,2'-biphenylene, $R_1$ as ferrocenyl may be unsubstituted or mono- or polysubstituted. This radical is preferably substituted on the same cyclopentadiene ring in the ortho position to the bonded P* by an $R_y$ group. This $R_y$ group may be vinyl, methyl, ethyl, or an ortho-directing, C-bonded chiral group which directs metals of metallating reagents into the ortho position, or a —CH$_2$—NR$_4$R$_5$ group in which $R_4$ and $R_5$ are each independently $C_1$-$C_8$-alkyl, $C_5$-$C_8$-Cycloalkyl, $C_6$-$C_{10}$-aryl, $C_7$-$C_{12}$-aralkyl, $C_7$-$C_{12}$-alkaryl, or $C_8$-$C_{12}$-alkaralkyl, or $R_4$ and $R_5$ together are tetramethylene, pentamethylene or 3-oxapentane-1,5-diyl. $R_4$ and $R_5$ are preferably identical radicals. $R_4$ and $R_5$ are preferably $C_1$-$C_4$-alkyl, cyclopentyl, cyclohexyl, phenyl, methylphenyl, methylbenzyl or benzyl, or $R_4$ and $R_5$ together are preferably tetramethylene or 3-oxapentane-1,5-diyl. More preferably, $R_4$ and $R_5$ are each methyl or ethyl.

The ortho-directing $R_y$ group may correspond to a chiral group, for example of the formula —HC*R$_6$R$_7$ (* indicates the asymmetric atom) in which $R_6$ is $C_1$-$C_8$-alkyl, $C_5$-$C_8$-cycloalkyl(cyclohexyl), $C_6$-$C_{10}$-aryl(phenyl), $C_7$-$C_{12}$-aralkyl (benzyl) or $C_7$-$C_{12}$-alkaralkyl(methylbenzyl), $R_7$ is —OR$_8$ or —NR$_4$R$_5$, $R_8$ is $C_1$-$C_8$-alkyl, $C_5$-$C_8$-cycloalkyl, phenyl or benzyl, and $R_4$ and $R_5$ are the same or different and are each $C_1$-$C_8$-alkyl, $C_5$-$C_8$-cycloalkyl, phenyl or benzyl, or $R_4$ and $R_5$ together with the nitrogen atom form a five- to eight-membered ring. $R_6$ is preferably $C_1$-$C_4$-alkyl, for example methyl, ethyl, n-propyl and phenyl. $R_8$ is preferably $C_1$-$C_4$-alkyl, for example methyl, ethyl, n-propyl and n- or i-butyl. $R_4$ and $R_5$ are preferably identical radicals and are preferably each $C_1$-$C_4$-alkyl, for example methyl, ethyl, n-propyl, i-propyl and n- or i-butyl, and together are tetramethylene, pentamethylene or 3-oxa-1,5-pentylene. Particularly preferred groups of the formula —HCR$_6$R$_7$ are 1-methoxyeth-1-yl, 1-dimethylaminoeth-1-yl and 1-(dimethylamino)-1-phenylmethyl.

A preferred subgroup of inventive compounds of the formula (I) is that of those in which Q when defined as arene or heteroarene is an unsubstituted radical, or one substituted as detailed above, of the formulae

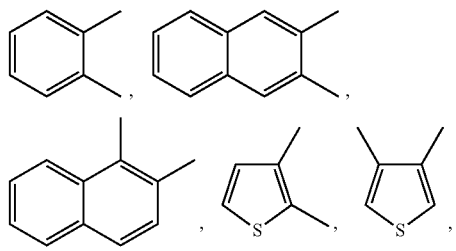

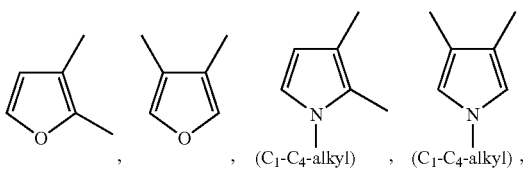

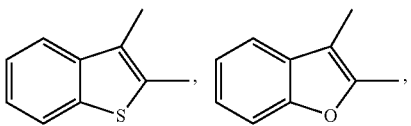

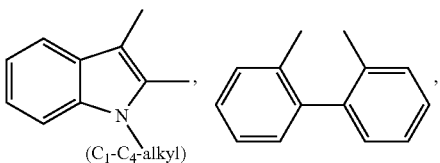

secondary phosphine is the —PR$_2$R$_3$ group in which R$_2$ and R$_3$ are each independently a hydrocarbon radical or an O-atom(s) containing heterohydrocarbon radical which has 1 to 18 carbon atoms and is unsubstituted or substituted by C$_1$-C$_6$-alkyl, trifluoromethyl, C$_1$-C$_6$-alkoxy, trifluoromethoxy, (C$_1$-C$_4$-alkyl)$_2$amino, (C$_6$H$_5$)$_3$Si, (C$_1$-C$_{12}$-alkyl)$_3$ Si, halogen; and the —PR$_2$R$_3$ group is bonded to the skeleton directly or via —CH$_2$—, —(CH$_2$)— or C$_2$-C$_6$-alkylidene; and R$_1$ is C$_1$-C$_8$-alkyl, cyclopentyl or cyclohexyl which are unsubstituted or substituted by 1 to 3 C$_1$-C$_4$-alkyl or C$_1$-C$_4$-alkoxy, or benzyl, phenyl, naphtyl or anthryl which are unsubstituted or substituted by 1 to 3 C$_1$-C$_4$-alkyl, C$_1$-C$_4$-alkoxy, C$_1$-C$_4$-fluoroalkyl or C$_1$-C$_4$-fluoroalkoxy, F or Cl, or R$_1$ is ferrocenyl which is unsubstituted or mono- or polysubstituted, preferably on the same cyclopentadiene ring in the ortho position to the bonded P* by an ortho-directing R$_y$ group.

In this preferred embodiment, Q is more preferably radicals of the formulae

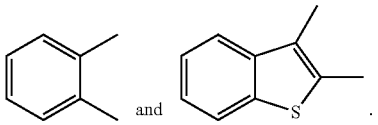

Another preferred subgroup of inventive compounds of the formula (I) is that of those in which Q when defined as 2,2'-biphenylene is unsubstituted radical, or one substituted as detailed above, of the formula

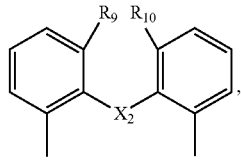

X$_2$ is a bond, —CH$_2$—, —(CH$_2$)$_2$—, C$_2$-C$_8$-alkylidene, cyclopentylidene, cyclohexylidene, —CH(O—C$_1$-C$_4$-alkyl)-, O—, —S—, —NR$_{07}$— or —Si(R$_{07}$)$_2$—;

R$_{07}$ is C$_1$-C$_4$-alkyl;

R$_9$ and R$_{10}$ are each a hydrogen atom, or R$_9$ and R$_{10}$ together are a bond or are —CH$_2$—, —(CH$_2$)$_2$— or C$_2$-C$_8$-alkylidene;

secondary phosphine is the —PR$_2$R$_3$ group in which R$_2$ and R$_3$ are each independently a hydrocarbon radical or an O-atom(s) containing heterohydrocarbon radical which has 1 to 18 carbon atoms and is unsubstituted or substituted by C$_1$-C$_6$-alkyl, trifluoromethyl, C$_1$-C$_6$-alkoxy, trifluoromethoxy, (C$_1$-C$_4$-alkyl)$_2$amino, (C$_6$H$_5$)$_3$Si, (C$_1$-C$_{12}$-alkyl)$_3$ Si, halogen and the —PR$_2$R$_3$ group is linked to the skeleton directly or via —CH$_2$—, —(CH$_2$)— or C$_2$-C$_6$-alkylidene; and R$_1$ is C$_1$-C$_8$-alkyl, cyclopentyl or cyclohexyl which are unsubstituted or substituted by 1 to 3 C$_1$-C$_4$-alkyl or C$_1$-C$_4$-alkoxy, or benzyl, phenyl, naphtyl or anthryl which are unsubstituted or substituted by 1 to 3 C$_1$-C$_4$-alkyl, C$_1$-C$_4$-alkoxy, C$_1$-C$_4$-fluoroalkyl or C$_1$-C$_4$-fluoroalkoxy, F or Cl, or R$_1$ is ferrocenyl which is unsubstituted or mono- or polysubstituted, preferably on the same cyclopentadiene ring in the ortho position to the bonded P* by an ortho-directing R$_y$ group.

A further preferred subgroup of inventive compounds of the formula (I) is that of those in which Q is unsubstituted 1,1'-ferrocenylene of the formula

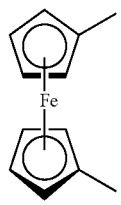

secondary phosphine is the —PR$_2$R$_3$ group in which R$_2$ and R$_3$ are each independently a hydrocarbon radical or an O-atom(s) containing heterohydrocarbon radical which has 1 to 18 carbon atoms and is unsubstituted or substituted by C$_1$-C$_6$-alkyl, trifluoromethyl, C$_1$-C$_6$-alkoxy, trifluoromethoxy, (C$_1$-C$_4$-alkyl)$_2$amino, (C$_6$H$_5$)$_3$Si, (C$_1$-C$_{12}$-alkyl)$_3$ Si, halogen and the —PR$_2$R$_3$ group is linked to the skeleton directly or via —CH$_2$—, —(CH$_2$)— or C$_2$-C$_6$-alkylidene; and R$_1$ is C$_1$-C$_8$-alkyl, cyclopentyl or cyclohexyl which are unsubstituted or substituted by 1 to 3 C$_1$-C$_4$-alkyl or C$_1$-C$_4$-alkoxy, or benzyl, phenyl, naphtyl or anthryl which are unsubstituted or substituted by 1 to 3 C$_1$-C$_4$-alkyl, C$_1$-C$_4$-alkoxy, C$_1$-C$_4$-fluoroalkyl or C$_1$-C$_4$-fluoroalkoxy, F or Cl, or R$_1$ is unsubstituted ferrocenyl.

A further preferred subgroup of inventive compounds of the formula (I) is that of those in which Q is unsubstituted or C$_1$-C$_4$-alkyl- or phenyl-substituted C$_1$-C$_4$-alkylene;

secondary phosphine is the —PR$_2$R$_3$ group in which R$_2$ and R$_3$ are each independently a hydrocarbon radical or an O-atom(s) containing heterohydrocarbon radical which has 1 to 18 carbon atoms and is unsubstituted or substituted by C$_1$-C$_6$-alkyl, trifluoromethyl, C$_1$-C$_6$-alkoxy, trifluoromethoxy, (C$_1$-C$_4$-alkyl)$_2$amino, (C$_6$H$_5$)$_3$Si, (C$_1$-C$_{12}$-alkyl)$_3$ Si, halogen;

and

R$_1$ is C$_1$-C$_8$-alkyl, cyclopentyl or cyclohexyl which are unsubstituted or substituted by 1 to 3 C$_1$-C$_4$-alkyl or C$_1$-C$_4$-alkoxy, or benzyl, phenyl, naphtyl or anthryl which are unsubstituted or substituted by 1 to 3 C$_1$-C$_4$-alkyl, C$_1$-C$_4$-alkoxy, C$_1$-C$_4$-fluoroalkyl or C$_1$-C$_4$-fluoroalkoxy, F or Cl, or R$_1$ is ferrocenyl which is unsubstituted or mono- or polysubstituted, preferably on the same cyclopentadiene ring in the ortho position to the bonded P* by an ortho-directing R$_y$ group.

Interesting compounds according to the invention are those selected from the group consisting of:

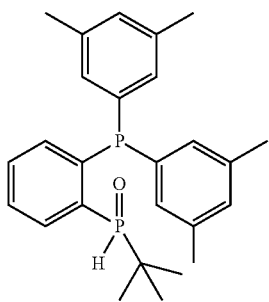

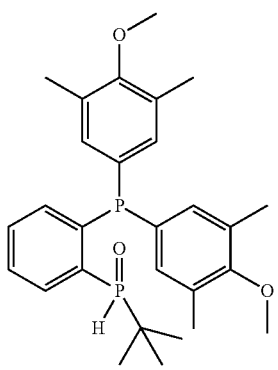

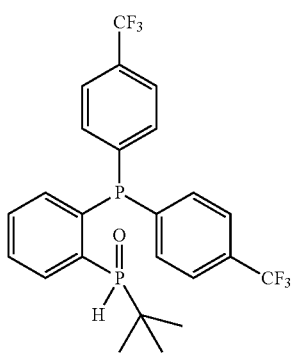

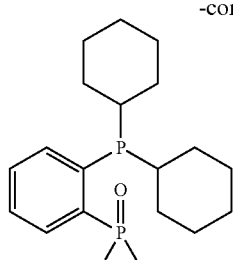

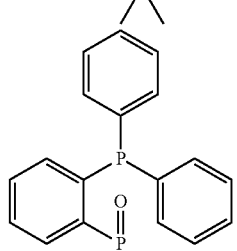

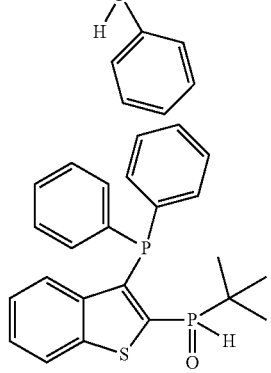

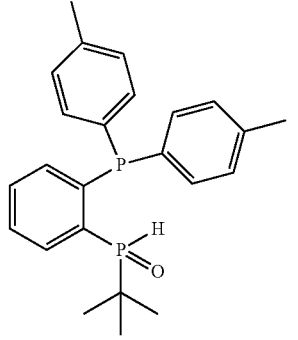

and

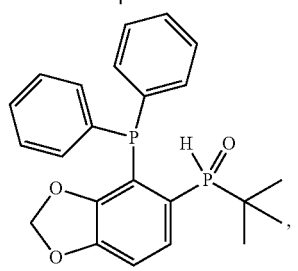

wherein the absolute configuration on the stereogenic P is R or S.

The inventive compounds of the formula (I) are obtainable in a simple manner from halogenated precursors, by first metallating the precursor, for example with lithium alkyl, then reacting the metallated compound with a dihalophosphine, a halomonoalkoxyphosphine or a halomono(dialkylamino)phosphine, and, in a last stage, forming the —*P (=O)HR$_1$ group. The reactions proceed with high yields and reaction products from the intermediate stages and the final stage can—if required—be purified by simple means, for example recrystallization and chromatographic purifications with achiral columns, for example on silica gels as the solid phase. In the recrystallization, it may be appropriate to convert the compounds of the formula (I) to phosphonium salts, for example with Cl$^-$, —Br$^-$, I$^-$, ClO$_4^-$, CF$_3$SO$_3^-$, CH$_3$SO$_3^-$, HSO$_4^-$, (CF$_3$SO$_2$)$_2$N$^-$, (CF$_3$SO$_2$)$_3$C$^-$ anions, tetraarylborates, for example B(phenyl)$_4^-$, B[bis(3,5-trifluoromethyl)phenyl]$_4^-$, B[bis(3,5-dimethyl)phenyl]$_4^-$, B(C$_6$F$_5$)$_4^-$ and B(4-methylphenyl)$_4^-$, or BF$_4^-$, PF$_6^-$, SbCl$_6^-$, AsF$_6^-$ or SbF$_6^-$. Enantiomers of intermediates and end products can also be obtained by chromatography on chiral columns or recrystallization, if appropriate from salts of achiral or chiral acids, for example phenyllactic acid or α-amino acids (see for example J. Drabowicz et al. in Tetrahedron: Asymmetry 10 (1999) 2757-63). Alternatively, it is also possible to purify compounds of formula (I) by formation and purification, e.g. by fractional crystallization, of metal complexes.

The invention further provides a process for preparing compounds of the formula I, characterized in that a compound of the formula II secondary phosphine-Q-Hal    (II)

in which secondary phosphine and Q are each as defined above and Hal is Cl, Br or I or an active hydrogen atom is reacted with a metallating reagent and then with a halophosphine of the formula (III)

R$_1$—P(Hal$_1$)$_2$    (III)

in which
R$_1$ is as defined above in formula I, including the preferences,
Hal$_1$ is Cl, Br or I,
and the compound of the formula (IV) formed secondary phosphine-Q-P Hal$_1$R$_1$    (IV)

is hydrolyzed with water to a racemic compound of the formula (I) which finally can be optically resolved by methods like chiral HPLC or by crystallization in presence of a chiral auxiliary to give the optically pure or enriched compound of the formula (I).

Alternatively, compounds of the formula (IV) can be reacted with a chiral, optically pure or enriched primary amine, secondary amine or alcohol, of the formula H—X*, In which H is hydrogen and X* is an optically enriched or optically pure chiral group of the formula G-C*R'R''R''', wherein
C* is an asymmetric carbon atom
G is O, HN or (R'''')N
R'''' is C$_1$-C$_8$-alkyl, C$_5$-C$_8$-cycloalkyl, in particular cyclohexyl, C$_6$-C$_{10}$-aryl, in particular phenyl, C$_7$-C$_{12}$-aralkyl, in particular benzyl, or C$_7$-C$_{12}$-alkaralkyl, in particular methylaralkyl, e.g. methylbenzyl,
R', R'', R''' are different and independently are a hydrogen radical, a hydrocarbon radical or a heterohydrocarbon radical,
to give diastereomerically enriched compounds of the formula (IV*)

secondary phosphine-Q-PX*R$_1$    (IV*).

The hydrocarbon radicals and heterohydrocarbon radicals as substituents in the chiral carbon atom C* may be unsubstituted or substituted and contain heteroatoms selected from the group of O, S, —N= and N(C$_1$-C$_4$-alkyl). They may contain 1 to 30, preferably 1 to 20, and more preferably 1 to 12 carbon atoms. The hydrocarbon radical or heterohydrocarbon radical may be selected from the group of linear or branched C$_1$-C$_{18}$-alkyl; unsubstituted or C$_1$-C$_6$-alkyl- or C$_1$-C$_6$-alkoxy-substituted C$_5$-C$_{12}$-cycloalkyl or C$_5$-C$_{12}$-cycloalkyl-CH$_2$—; phenyl, naphthyl, furyl or benzyl; or halogen-, C$_1$-C$_6$-alkyl-, trifluoromethyl-, C$_1$-C$_6$-alkoxy-, trifluoromethoxy-, (C$_6$H$_5$)$_3$Si—, (C$_1$-C$_{12}$-alkyl)$_3$Si—, or secondary amino-substituted phenyl, naphthyl, furyl or benzyl.

Two radicals R' and R'' can form a 4 to 12 membered monocyclic or polycyclic hydrocarbon ring which has a stereogenic carbon atom at least in the a position to the G/C bond.

Two radicals R' and R'''' can form a 4 to 12 membered monocyclic or polycyclic hydrocarbon ring.

Preferred X* are the following groups:

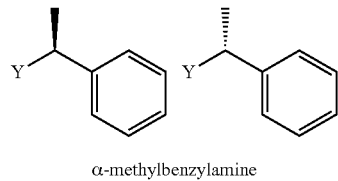

α-methylbenzylamine

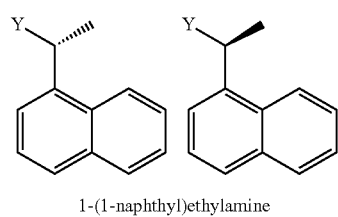

1-(1-naphthyl)ethylamine

Y = HO, H2N, alkyl(H)N, Aralkyl(H)N, aryl(H)N

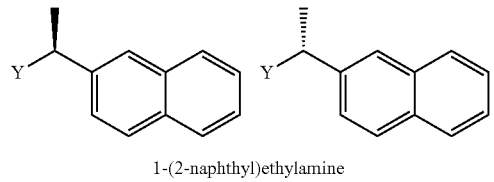

1-(2-naphthyl)ethylamine

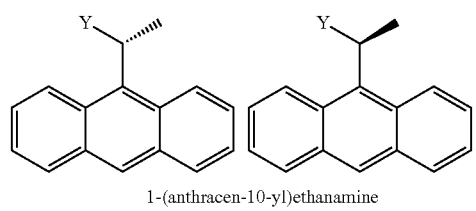

1-(anthracen-10-yl)ethanamine

-continued
Y = HO, H2N, alkyl(H)N, Aralkyl(H)N, aryl(H)N

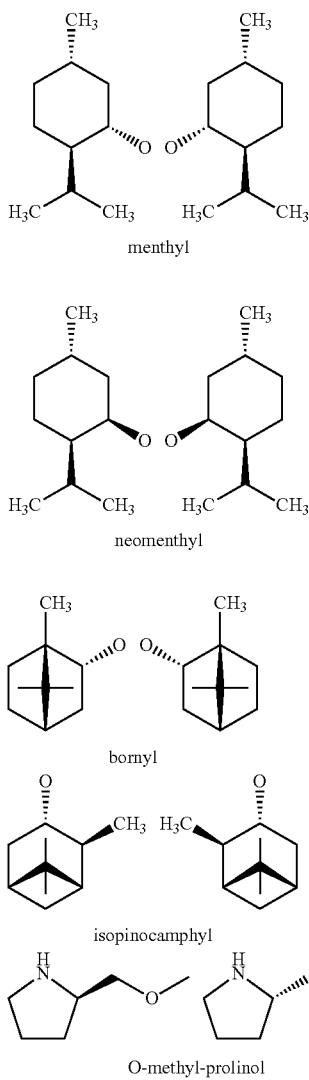

menthyl neomenthyl bornyl isopinocamphyl and

O-methyl-prolinol

Optionally, the compounds of the formula (IV*) can be further diastereomerically enriched by known methods such as chromatography or recrystallization.

The compounds of the formula (IV*) are then hydrolyzed or treated with a neat acid, e.g. pure formic acid, to give optically enriched compounds of the formula (I). Optically pure compounds of formula (I) can be obtained by repeated recrystallization.

The invention also concerns the new compounds of the formula (IV*)

secondary phosphine-Q-PX*R$_1$ (IV*), where X* is an optically enriched or optically pure chiral group of the formula G-C*'R"R''', with the preferences mentioned above, wherein C* is an asymmetric carbon atom
G is O, HN or (R"")N
R"" is $C_1$-$C_8$-alkyl, $C_5$-$C_8$-cycloalkyl, in particular cyclohexyl, $C_6$-$C_{10}$-aryl, in particular phenyl, $C_7$-$C_{12}$-aralkyl, in particular benzyl, or $C_7$-$C_{12}$-alkaralkyl, in particular methylaralkyl, e.g. methylbenzyl, R', R", R''' are different and independently are a hydrogen radical, a hydrocarbon radical or a heterohydrocarbon radical, which are useful as intermediates in the preparation of the compounds of formula (I).

Compounds of the formula (II) are known or can be prepared by known or analogous processes.

α-Methylbenzyloxy, α-methylbenzylamine, menthyloxy and the bivalent —O—CHR$_t$—CHR$_u$—NR$_v$— group derive from chiral auxiliary reagents, and it is possible, for example, to enrich and/or separate diastereomeric intermediate compounds of the formula (IV*) by known techniques, in order to achieve the formation of predominantly one enantiomer in the hydrolysis thereof (see Examples B7 and B8). Such methods are known in the literature to work with simpler SPO containing compounds (such as tert.-butylphenylphosphineoxide) and are described, for example, by G. Buono et al. in THL 46 (2005), 8677-80 and THL 48 (2007), 5247-50, by S. Jugé et al. in Tetrahedron: Asymmetry: 10 (1999), 4729-43 and by O. I. Kolodiazhnyi et. al in Tetrahedron: Asymmetry: 7 (1996), 967-70 or Tetrahedron: Asymmetry: 14 (2003), 181-3.

The process conditions are known for organometallic syntheses and are not described in detail here. Details can be taken from the examples.

The inventive compounds of the formula (I) are ligands for metal complexes selected from the group of the transition metals, which are outstanding catalysts or catalyst precursors for asymmetric syntheses, for example the asymmetric hydrogenation of prochiral, unsaturated, organic compounds. When prochiral, unsaturated, organic compounds are used, a very high excess of optical isomers can be induced in the synthesis of organic compounds and a high chemical conversion can be achieved within short reaction times. The achievable enantioselectivities and catalyst activities are excellent. In addition, such ligands can also be used in other asymmetric addition or cyclization reactions.

The invention further provides metal complexes of transition metals of the transition groups of the Periodic Table of the Elements with a compound of the formula (I) or of the formula A as ligands, where the molar ratio of ligand to metal is about 1.3:1 to 0.9:1 and preferably 1.1:1 to 0.9:1. More preferably, the equivalents ratio is about 1:1.

Among the transition metals, particular preference is given to metals selected from the group of Fe, Co, Ni, Cu, Ag, Au, Ru, Rh, Pd, Os, Ir. Very particularly preferred metals are Cu, Pd, Ru, Rh, Ir and Pt. Examples of organic syntheses are, as well as asymmetric hydrogenations von prochiral, unsaturated, organic compounds, amine couplings, enantioselective ring openings and hydrosilylations.

Particularly preferred metals are ruthenium, rhodium and iridium.

According to the oxidation number and coordination number of the metal atom, the metal complexes may contain further ligands and/or anions. They may also be cationic metal complexes. Such analogous metal complexes and their preparation have been described many times in the literature.

The metal complexes may, for example, correspond to the general formulae (V) and (VI)

$$A_1MeL_n \quad (V)$$

$$(A_1MeL_n)^{(z+)}(E^-)_z \quad (VI)$$

in which A₁ is a compound of the formula (I) or of the formula (A),

L represents identical or different monodentate, anionic or nonionic ligands, or two L represent identical or different bidentate, anionic or nonionic ligands;

n is 2, 3 or 4 when L is a monodentate ligand, or n is 1 or 2 when L is a bidentate ligand;

z is 1, 2 or 3;

Me is a metal selected from the group of Rh, Ir and Ru; where the metal has the oxidation states of 0, 1, 2, 3 or 4;

E is the anion of an oxygen acid or complex acid; and the anionic ligands balance the charge of the 1, 2, 3 or 4 oxidation states of the metal.

For the compounds of the formulae (I), the preferences and embodiments described above apply.

Monodentate nonionic ligands may, for example, be selected from the group of the olefins (for example ethylene, propylene), allyls (allyl, 2-methallyl), solvating solvents (nitriles, linear or cyclic ethers, optionally N-alkylated amides and lactams, amines, phosphines, alcohols, carboxylic esters, sulphonic esters), nitrogen monoxide and carbon monoxide.

Monodentate anionic ligands may, for example, be selected from the group of halide (F, Cl, Br, I), pseudohalide (cyanide, cyanate, isocyanate) and anions of carboxylic acids, sulphonic acids and phosphonic acids (carbonate, formate, acetate, propionate, methylsulphonate, trifluoromethylsulphonate, phenylsulphonate, tosylate).

Bidentate nonionic ligands may, for example, be selected from the group of the linear and cyclic diolefins (for example hexadiene, cyclooctadiene, norbornadiene), dinitriles (malonitrile), optionally N-alkylated carboxamides, diamines, diphosphines, diols, acetonylacetonates, dicarboxylic diesters and disulphonic diesters.

Bidentate anionic ligands may, for example, be selected from the group of the anions of dicarboxylic acids, disulphonic acids and diphosphonic acids (for example from oxalic acid, malonic acid, succinic acid, maleic acid, methylenedisulphonic acid and methylenediphosphonic acid).

Preferred metal complexes are also those in which E represents anions of oxygen acids selected from the group of $ClO_4^-$, $CF_3SO_3^-$, $CH_3SO_3^-$, $HSO_4^-$, and anions of complex acids selected from the group of tetraarylborates, for example $B(phenyl)_4^-$, $B[bis(3,5-trifluoromethyl)phenyl]_4^-$, $B[bis(3,5-dimethyl)phenyl]_4^-$, $B(C_6F_5)_4^-$ and $B(4-methylphenyl)_4^-$, and $BF_4^-$, $PF_6^-$, $SbCl_6^-$, $AsF_6^-$ or $SbF_6^-$. Other suitable anions E⁻ are —Cl⁻, —Br⁻, —I⁻, $(CF_3SO_2)_2N^-$ and $(CF_3SO_2)_3C^-$.

Especially preferred metal complexes which are particularly suitable for hydrogenations correspond to the formulae VII and VIII

[A₁Me₂YZ]  (VII)

[A₁Me₂Y]⁺E₁⁻  (VIII)

in which

A₁ is a compound of the formula (I) or the formula (A);

Me₂ is rhodium or iridium;

Y represents two olefins or one diene;

Z is Cl, Br or I; and

E₁⁻ is the anion of an oxygen acid or complex acid.

For the compounds of the formula (I), the preferences and embodiments described above apply.

When Y is defined as olefin, it may be $C_2$-$C_{12}$—, preferably $C_2$-$C_6$— and more preferably $C_2$-$C_4$-olefins. Examples are propene, but-1-ene and particularly ethylene. The diene may contain 5 to 12 and preferably 5 to 8 carbon atoms, and the dienes may be open-chain, cyclic or polycyclic dienes. The two olefin groups of the diene are preferably connected by one or two $CH_2$ groups. Examples are 1,3-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene and norbornadiene. Y preferably represents two ethylene or 1,5-hexadiene, 1,5-cyclooctadiene or norbornadiene.

In formula (VIII), Z is preferably Cl or Br. Examples of $E_1^-$ are $BF_4^-$, $ClO_4^-$, $CF_3SO_3^-$, $CH_3SO_3^-$, $HSO_4^-$, $B(phenyl)_4^-$, $B[bis(3,5-trifluoromethyl)phenyl]_4^-$, $PF_6^-$, $SbCl_6^-$, $AsF_6^-$ or $SbF_6^-$.

The inventive metal complexes are prepared by methods known in the literature (see also U.S. Pat. Nos. 5,371,256, 5,446,844, 5,583,241, and E. Jacobsen, A. Pfaltz, H. Yamamoto (Eds.), Comprehensive Asymmetric Catalysis I to III, Springer Verlag, Berlin, 1999, and literature cited therein).

The inventive metal complexes are homogeneous catalysts or catalyst precursors activable under the reaction conditions, which can be used for asymmetric addition reactions onto prochiral, unsaturated, organic compounds; see E. Jacobsen, A. Pfaltz, H. Yamamoto (Eds.), Comprehensive Asymmetric Catalysis I to III, Springer Verlag, Berlin, 1999, and B. Cornils et al., in Applied Homogeneous Catalysis with Organometallic Compounds, Volume 1, Second Edition, Wiley VCH-Verlag (2002). Further applications are, for example, the amination of aromatics or heteroaromatics which contain leaving groups, for example halide or sulphonate, with primary or secondary amines using palladium complexes, or the preferably Rh-catalysed enantioselective ring-opening reaction of oxabicyclic alkanes (M. Lautens et al. in Acc. Chem. Res. Volume 36 (203), pages 48-58.

The metal complexes can, for example, be used for asymmetric hydrogenation (addition of hydrogen) of prochiral compounds with carbon/carbon or carbon/heteroatom double bonds. Such hydrogenations with soluble homogeneous metal complexes are described, for example, in Pure and Appl. Chem., Vol. 68, No. 1, pp. 131-138 (1996). Preferred unsaturated compounds for hydrogenation contain die C═C (prochiral alkenes), C═N (prochiral ketimines), C═N—N (prochiral ketohydrazones), C═N—O (prochiral ketoximes) and/or C═O (prochiral ketones) groups. For the hydrogenation, according to the invention, preference is given to using metal complexes of ruthenium, rhodium and iridium.

The invention further provides for the use of the inventive metal complexes as homogeneous catalysts for preparing chiral organic compounds by asymmetric addition of hydrogen onto a carbon- or carbon-heteroatom double bond in prochiral organic compounds.

A further aspect of the invention is a process for preparing chiral organic compounds by asymmetric addition of hydrogen onto a carbon or carbon-heteroatom double bond in prochiral organic compounds in the presence of a catalyst, characterized in that the addition is carried out in the presence of catalytic amounts of at least one metal complex of the invention.

Preferred prochiral, unsaturated compounds for hydrogenation may contain one or more, identical or different C═C, C═N and/or C═O groups, in open-chain or cyclic organic compounds, where the C═C, C═N and/or C═O groups may be part of a ring system or are exocyclic groups. The prochiral unsaturated compounds may be alkenes, cycloalkenes, heterocycloalkenes, and open-chain or cyclic ketones, α,β-diketones, α- or β-ketocarboxylic acids, and the α,β-keto acetals or ketals thereof, esters and amides, ketimines, ketoximes and kethydrazones. Alkenes, cycloalkenes, heterocycloalkenes also include enamides.

The process according to the invention can be carried out at low or elevated temperatures, for example temperatures of −20 to 150° C., preferably of −10 to 100° C., and more preferably of 10 to 80° C. The optical yields are generally better at lower temperature than at higher temperatures.

The process according to the invention can be carried out at standard pressure or elevated pressure. The pressure may, for example, be $10^5$ to $2 \times 10^7$ Pa (pascals). Hydrogenations can be carried out at standard pressure or elevated pressure.

Catalysts are preferably used in amounts of 0.00001 to 10 mol %, more preferably 0.00001 to 5 mol %, and especially preferably 0,00001 to 2 mol %, based on the compound to be hydrogenated.

The preparation of the ligands and catalysts and the hydrogenation can be carried out without or in the presence of an inert solvent, it being possible to use one solvent or mixtures of solvents. Suitable solvents are, for example, aliphatic, cycloaliphatic and aromatic hydrocarbons (pentane, hexane, petroleum ether, cyclohexane, methylcyclohexane, benzene, toluene, xylene), aliphatic halohydrocarbons (methylene chloride, chloroform, di- and tetrachloroethane), nitriles (acetonitrile, propionitrile, benzonitrile), ethers (diethyl ether, dibutyl ether, t-butyl methyl ether, ethylene glycol dimethyl ether, ethylene glycol diethyl ether, diethylene glycol dimethyl ether, tetrahydrofuran, dioxane, diethylene glycol monomethyl or monoethyl ether), ketones (acetone, methyl isobutyl ketone), carboxylic esters and lactones (ethyl or methyl acetate, valerolactone), N-substituted lactams (N-methylpyrrolidone), carboxamides (dimethylacetamide, dimethylformamide), acyclic ureas (dimethylimidazoline), and sulphoxides and sulphones (dimethyl sulphoxide, dimethyl sulphone, tetramethylene sulphoxide, tetramethylene sulphone) and optionally fluorinated alcohols (methanol, ethanol, propanol, butanol, ethylene glycol monomethyl ether, ethylene glycol monoethyl ether, diethylene glycol monomethyl ether, 1,1,1-trifluoroethanol) and water. Suitable solvents are also low molecular weight carboxylic acids, for example acetic acid.

The reactions can be carried out in the presence of cocatalysts, for example quaternary ammonium halides (tetrabutylammonium chloride, bromide or iodide) or protic acids, for example mineral acids such as HCl or strong organic acids such as trifluoroacetic acid, or mixtures of such halides and acids (see for example U.S. Pat. Nos. 5,371,256, 5,446,844 and 5,583,241 and EP-A-0 691 949). The presence of fluorinated alcohols, for example 1,1,1-trifluoroethanol, can also promote the catalytic reaction. The addition of bases, for example tertiary amines or phosphines, alkali metal hydroxides, secondary amides, alkoxides, carbonates and hydrogencarbonates may be advantageous. The selection of a cocatalyst may be guided principally by the metal in the metal complex and the substrate. In the hydrogenation of prochiral aryl ketimines, the use of iridium complexes in combination with tetra-$C_1$-$C_4$-alkylammonium iodides and mineral acids, preferably HI, has been found to be useful.

The metal complexes used as catalysts can be added as separately prepared isolated compounds, or else be formed in situ before the reaction and then mixed with the substrate to be hydrogenated. It may be advantageous to additionally add ligands in the case of reaction using isolated metal complexes, or to use an excess of the ligands in the case of in situ preparation. The excess may, for example, be 1 to 6 and preferably 1 to 2 mol, based on the metal compound used for the preparation.

The process according to the invention is generally carried out by initially charging the catalyst and then adding the substrate, optionally reaction assistants and the compound to be added on, and then starting the reaction. Gaseous compounds to be added on, for example hydrogen, are preferably injected. The process can be carried out in various reactor types, continuously or batchwise.

The chiral organic compounds preparable in accordance with the invention are active substances or intermediates for preparing such substances, especially in the sector of production of aromas and odorants, pharmaceuticals and agrochemicals.

The examples which follow illustrate the invention. All reactions are carried out under argon with exclusion of air and with degassed solvents. The yields are not optimized. Abbreviations: THF=tetrahydrofuran; TBME=tert-butyl methyl ether; nbd=norbornadiene; cod=cycloocta-1,5-diene.

A) PREPARATION OF LIGANDS

The compound o-bromophenyldiphenylphosphine is commercially available. The compound o-bromophenyldicyclohexylphosphine is prepared as described by M. Murata et al., Tetrahedron, 60 (2004) 7397-7403. The synthesis of 3-diphenylphosphine-benzothiophene is described in M. Kesselgruber et al., WO 2006/111535 and the synthesis of o-bromophenyl-di-para-tolylphosphine in J. F. Hartwig et al., J. Amer. Chem. Soc, 129 (2007) 7734.

Example A1

Preparation of
o-bromophenylbis(3,5-dimethylphenyl)phosphine
A1

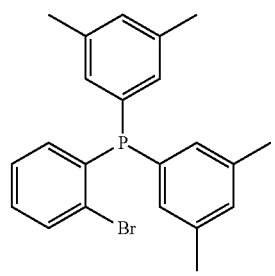

A1

To a solution of 9.67 g (34.2 mmol) of 1-bromo-2-iodobenzene in 30 ml of THF are added dropwise, at −78° C., 17.6 ml (37.6 mmol) of an isopropylmagnesium chloride solution (2 molar in THF). The mixture is stirred at a temperature between −30° C. and −40° C. for a further 1 hour, then cooled again to −78° C., and a suspension of 10.4 g (37.6 mmol) of bis(3,5-dimethylphenyl)chlorophosphine in 10 ml of THF and 10 ml of TBME are added. The cooling is removed and the reaction mixture is stirred at room temperature overnight. The resulting solution is admixed with 50 ml of water and extracted with water/TBME. The organic phases are collected and dried over sodium sulphate, and the solvent is distilled off under reduced pressure on a rotary evaporator. The solid white crude product is purified by chromatography (silica gel 60; eluent=methylene chloride). The desired product is obtained as a white solid in a yield of 56%.

$^{31}$P NMR (C$_6$D$_6$, 121 MHz): δ −3.46 (s); $^1$H NMR (C$_6$D$_6$, 300 MHz), characteristic signals: δ 7.43-6.6 (various m, 10H), 1.99 (s, 12H).

Example A2

Preparation of o-bromophenylbis(3,5-dimethyl-4-methoxyphenyl)-phosphine A2

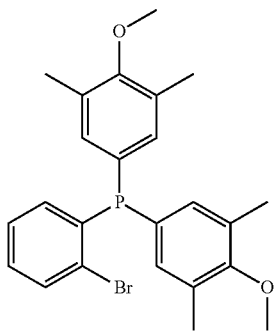

A2

Compound A2 is prepared analogously to compound A1. Instead of the bis(3,5-dimethylphenyl)chlorphosphine, the same molar amount of bis(3,5-dimethyl-4-methoxyphenyl) chlorophosphine is used. The crude product is purified by chromatography (silica gel 60; eluent=1:1 heptane/ethyl acetate). The desired product is obtained in the form of white crystals in a yield of 76%.

$^{31}$P NMR (C$_6$D$_6$, 121 MHz): δ −5.2 (s); $^1$H NMR (C$_6$D$_6$, 300 MHz), characteristic signals: δ 7.44-6.6 (various m, 8 H), 3.28 (s, 6H), 2.06 (s, 12H).

Example A3

Preparation of o-bromophenyl-bis(4-trifluoromethylphenyl)phosphine A3

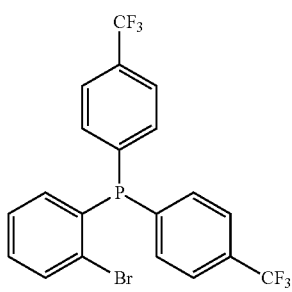

A3

Compound A3 is prepared analogously to compound A1. Instead of the bis(3,5-dimethylphenyl)chlorophosphine, the same molar amount of bis(4-trifluoromethyl-phenyl)chlorophosphine is used. The crude product is recrystallized in ethanol. The desired product is obtained in the form of white crystals in a yield of 90%.

$^{31}$P NMR (C$_6$D$_6$, 121 MHz): δ −4.8 (s); $^1$H NMR (C$_6$D$_6$, 300 MHz), characteristic signals: δ 7.25-6.4 (various m, 12 H).

Example A4

Preparation of 4-bromo-3-diphenylphosphino-1,2-methylenedioxy)benzene A4

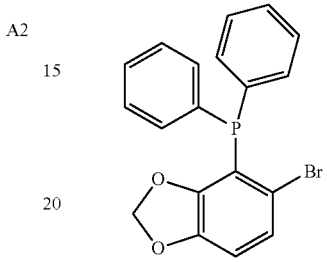

A4

To a solution of 55 mmol lithiumdiisopropylamide (freshly prepared from 55 mmol diisopropylamine and 55 mmol n-BuLi (1.6M in hexane) in 115 ml THF) are added dropwise, at −78° C. within 10 minutes, 6.02 ml (50 mmol) 4-bromo-1,2-(methylenedioxy)benzene. After stirring for 1 hour at approx. −70° C., 10.16 ml (55 mmol) chlorodiphenylphosphine are added dropwise within 30 minutes. After stirring for 1 hour at the same temperature, the temperature is allowed to rise to room temperature. After addition of 25 ml water and 100 ml ethylacetate, HCl 2N is added until the water phase is slightly acidic. The organic phase is separated, washed with Na$_2$CO$_3$, dried over Na$_2$SO$_4$ and the solvent is distilled off on a rotary evaporator. The raw product is suspended and stirred in boiling TBME and, after cooling to room temperature filtered and washed with heptane. The obtained solid product is almost white and sufficiently pure for further use. If required, it can be further purified by column chromatography (silica gel 60; eluent=5:1 heptane/toluene). The product A4 is obtained in the form of colourless crystals in a yield of 70%.

$^{31}$P NMR (C$_6$D$_6$, 121 MHz): δ −5.12 (s); $^1$H NMR (C$_6$D$_6$, 300 MHz), characteristic signals: δ 7.51 (m, 4H), 7.07 (m, 6H), 6.92 (d of d, 1H), 6.25 (d, 1H), 4.83 (s, 2H).

B) PREPARATION OF LIGANDS

Example B1

Preparation of Ligand B1

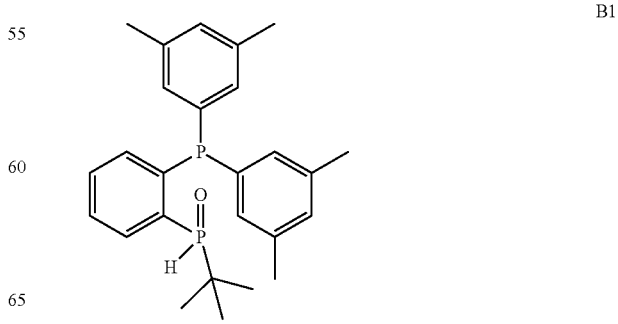

B1

To a solution of 2.3 g (5.8 mmol) of compound A1 in 5 ml of THF and 5 ml of TBME are added dropwise, at −78° C., 3.8 ml (5.8 mmol) of n-butyllithium (1.6 M in hexane). The mixture is stirred at −78° C. for a further 2 hours. The reaction solution is then transferred with the aid of a cannula using elevated argon pressure into a reaction vessel in which a solution of 0.92 g (5.8 mmol) of tert-butyldichlorophosphine in 5 ml of TBME is being stirred 0° C. After 1.5 hours, the cooling is removed and the white suspension is stirred further at room temperature overnight. 50 ml of water and 5 ml of 2 molar NaOH are added. After stirring for 40 minutes, the mixture is extracted with water/TBME. The organic phases are collected and dried over sodium sulphate, and the solvent is distilled off on a rotary evaporator under reduced pressure. The white solid crude product is purified by chromatography (silica gel 60; eluent=heptane/ethyl acetate). The desired racemic ligand B1 is obtained as a white solid in a yield of 59%.

The two enantiomers of B1 can be separated with the aid of semipreparative HPLC with a chiral column (Chiracel OD, 2*25 cm). Conditions: hexane/isopropanol 99:1, 6 ml/min, 25° C. Retention times: enantiomer 1=66 min.; enantiomer 2=86 min.

$^{31}$P NMR of enantiomer 1 (C$_6$D$_6$, 121 MHz): δ 34.6 (d, J=48 Hz), −11.8 (d, 48 Hz)

$^1$H NMR of enantiomer 1 (C$_6$D$_6$, 300 MHz), characteristic signals: δ 8.24 (dd, J=461 Hz, J=4.6 Hz, 1H), 8.16-8.07 (m, 1H), 7.36-7.29 (m, 1H), 7.19-6.7 (various m, 8H), 2.00 (s, 6H), 1.98 (s, 6H), 1.16 (d, 9H).

Example B2

Preparation of Ligand B2

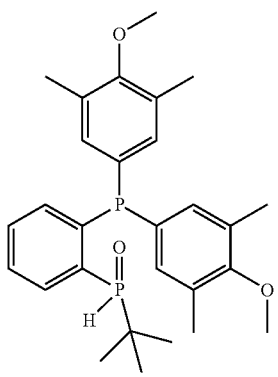

B2

To a solution of 2.96 g (6.48 mmol) of compound A2 in 5 ml of THF and 5 ml of TBME are added dropwise, at −78° C., 4.05 ml (6.48 mmol) of n-butyllithium (1.6 M in hexane). The mixture is stirred at −78° C. for a further 2 hours. The reaction solution is then transferred with the aid of a cannula using elevated argon pressure into a reaction vessel in which a solution of 1.03 g (6.48 mmol) of tert-butyldichlorophosphine in 5 ml of TBME is being stirred at 0° C. After 1.5 hours, the cooling is removed and the white suspension is stirred at room temperature for a further 2 hours. 50 ml of water and 5 ml of 2 molar NaOH are then added. After stirring for 40 minutes, the mixture is extracted with water/TBME. The organic phases are collected and dried over sodium sulphate, and the solvent is distilled off under reduced pressure on a rotary evaporator. The white solid crude product is purified by chromatography (silica gel 60; eluent=ethyl acetate). The desired racemic ligand B2 is obtained as a white solid in a yield of 65%.

The two enantiomers of B2 can be separated with the aid of semipreparative HPLC with a chiral column (Chiracel OD, 2*25 cm). Conditions: hexane/isopropanol 99:1, 6 ml/min, 40° C. Retention times: enantiomer 1=112 min.; enantiomer 2=155 min.

$^{31}$P NMR of enantiomer 1 (C$_6$D$_6$, 121 MHz): δ 34.7 (d, J=60 Hz), −13.6 (d, 60 Hz)

$^1$H NMR of enantiomer 1 (C$_6$D$_6$, 300 MHz), characteristic signals: δ 8.25 (dd, J=462 Hz, J=4.5 Hz, 1H), 8.15-8.07 (m, 1H), 7.42-7.36 (m, 1H), 7.27-7.0 (various m, 6H), 3.27 (d, 6H), 2.06 (d, 12H), 1.18 (d, 9H).

Example B3

Preparation of Ligand B3

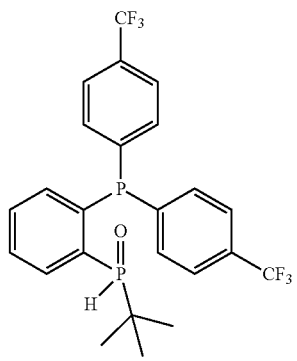

B3

Compound B3 is prepared analogously to compound B1 proceeding from compound A3. The crude product is purified by chromatography (silica gel 60; eluent=ethyl acetate). The racemic ligand B3 is obtained as a white solid in a yield of 61%. The two enantiomers of B3 can be separated with the aid of semipreparative HPLC with a chiral column (Chiracel OD, 2*25 cm). Conditions: hexane/isopropanol 98.5: 1.5, 6 ml/min, 40° C. Retention times: enantiomer 1=77 min.; enantiomer 2=86 min.

$^{31}$P NMR of enantiomer 1 (C$_6$D$_6$, 121 MHz): δ 39.7 (d), −12.1 (d); $^1$H NMR of enantiomer 1 (C$_6$D$_6$, 300 MHz), characteristic signals: δ 8.50 (d, ½H), 7.8-7.71 (m, 1H), 7.25-6.89 (various m, 11.5H), 1.08 (d, 9H).

Example B4

Preparation of Ligand B4

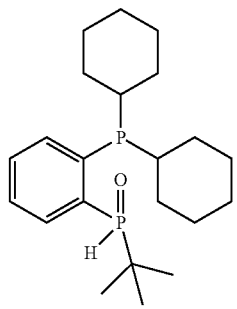

B4

Compound B4 is prepared analogously to compound B1 proceeding from o-bromo-phenyldicyclohexylphosphine. The crude product is purified by chromatography (silica gel 60; eluent=ethyl acetate). The racemic ligand B4 is obtained as a white solid in a yield of 55%.

The two enantiomers of B4 can be separated with the aid of semipreparative HPLC with a chiral column.

$^{31}$P NMR (C$_6$D$_6$, 121 MHz): δ 34.5 (d), −13.6 (d); $^1$H NMR (C$_6$D$_6$, 300 MHz), characteristic signals: δ 8.61 (dd, J=493 Hz, J=6 Hz, 1H), 8.21-8.13 (m, 1H), 7.37-7.30 (m, 1H), 7.14-7.07 (m, 2H), 2.1-08 (m, 22H), 1.16 (d, 9H).

Example B5

Preparation of Ligand B5

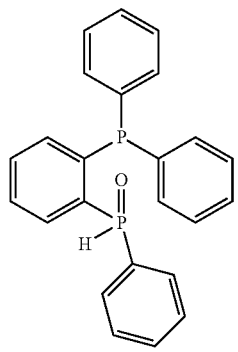

B5

To a solution of 2.6 g (7.6 mmol) of the compound o-bromophenyldiphenylphosphine in 6 ml of THF and 6 ml of TBME are added dropwise, at −78° C., 4.8 ml (7.6 mmol) of n-butyllithium (1.6 M in hexane). The mixture is stirred at −78° C. for a further 2 hours. The reaction mixture is then transferred with the aid of a cannula using elevated argon pressure into a reaction vessel in which a solution of 1.03 ml (7.6 mmol) of P,P-dichlorophenylphosphine in 6 ml of TBME is being stirred at 0° C. The flask and the cannula are washed with a further 5 ml of THF. After 1.5 hours, the cooling is removed. 50 ml of water are then added. After stirring for 70 minutes, 20 ml of saturated aqueous NaCl are added, and the mixture is extracted first with 10:1 ethyl acetate/methylene chloride, then ethyl acetate, toluene and finally methylene chloride. The organic phases are collected and dried over sodium sulphate, and the solvent is distilled off on a rotary evaporator under reduced pressure. The white solid crude product is purified by chromatography (silica gel 60; eluent=ethyl acetate). The racemic ligand B5 is obtained as a white solid in a yield of 73%.

The two enantiomers of B5 can be separated with the aid of semipreparative HPLC with a chiral column (Chiracel OD, 2*25 cm). Conditions: 90:10 hexane/isopropanol, 6 ml/min, 20° C. Retention times: enantiomer 1=78 min.; enantiomer 2=85 min.

$^{31}$P NMR of enantiomer 1 (C$_6$D$_6$, 121 MHz): δ 13.7 (d), −17.0 (d); $^1$H NMR of enantiomer 1 (C$_6$D$_6$, 300 MHz), characteristic signals: δ 8.83 (dd, J=501 Hz, J=3.9 Hz, 1H), 8.31-8.23 (m, 1H), 7.61-7.52 (m, 2H), 7.16-6.84 (various m, 16H).

Example B6

Preparation of Ligand B6

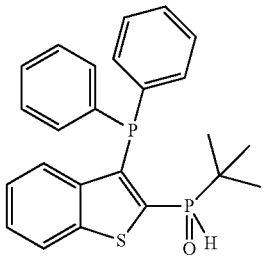

B6

To a solution of 0.97 g (3.05 mmol) of 2-diphenylphosphinobenzothiophene in 4 ml of diethyl ether and 0.48 ml (3.05 mmol) of N,N,N',N'-tetramethylethylenediamine are added dropwise 1.94 ml (3.05 mmol) of n-butyllithium (1.6 M in hexane). The reaction mixture is stirred further overnight and then transferred with the aid of a cannula using elevated argon pressure into a reaction vessel in which a solution of 0.48 g (3.05 mmol) of tert-butyldichlorophosphine in 2 ml of diethyl ether is being stirred. After 40 minutes, 20 ml of water, 2 ml of 2N NaOH and 10 ml of THF are added and the mixture is stirred vigorously over 5 hours. Subsequently, 10 ml of saturated aqueous NaCl solution are added and the mixture is extracted with ethyl acetate. The organic phases are collected and dried over sodium sulphate, and the solvent is distilled off under reduced pressure on a rotary evaporator. The crude product is purified by chromatography (silica gel 60; eluent=heptane/ethyl acetate). The racemic ligand B6 is obtained as a white solid in a yield of 34%.

The two enantiomers of B6 can be separated with the aid of semipreparative HPLC with a chiral column (Chiracel OD, 2*25 cm). Conditions: hexane/isopropanol 95:5, 6 ml/min, 40° C. Retention times: enantiomer 1=131 min.; enantiomer 2=144 min.

$^{31}$P NMR of enantiomer 1 (C$_6$D$_6$, 121 MHz): δ 31.7 (d), −26.1 (d); $^1$H NMR of enantiomer 1 (C$_6$D$_6$, 300 MHz), characteristic signals: δ 8.49 (dd, J=483 Hz, J=5.4 Hz, 1H), 7.5-6.72 (various m, 14H), 1.10 (d, 9H).

Example B7

Stereoselective Synthesis of Ligand B7

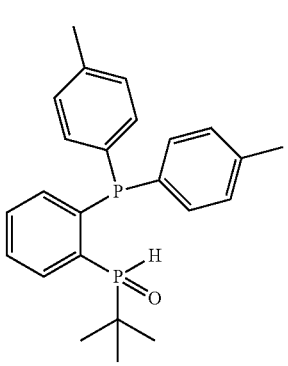

B7

To a solution of 2.33 g (6.32 mmol) of o-bromophenyl-di-para-tolylphosphine in 12 ml of THF are added dropwise, at −78° C., 4.0 ml (6.3 mmol) of n-butyllithium (1.6 M in hexane). The mixture is stirred at −78° C. for 1 hour. The reaction solution is then transferred with the aid of a cannula using elevated argon pressure into a reaction vessel in which a solution of 0.99 g (6.3 mmol) of tert-butyldichlorophosphine in 3 ml of THF is being stirred at −78° C. The cooling is removed and the mixture is stirred further at room temperature for 1.5 hour before the solvent is distilled off at 45° C. on a rotary evaporator under reduced pressure. Then 12 ml toluene and 1.4 ml of $NEt_3$ are added to the residue. To the resulting turbid solution, 0.81 ml (6.3 mmol) of (S)-(−)-alpha-methylbenzylamine are added and the mixture stirred at room temperature for several days, until formation of the aminophosphine intermediate I7 is complete. Then, the reaction mixture is extracted with water and toluene. The organic phases are collected, dried over $Na_2SO_4$ and the solvent distilled off on a rotary evaporator under reduced pressure. 3.1 g of a crude viscous product are obtained which according to $^{31}$P-NMR consists, of an approx. 15:1 mixture of a major and a minor epimer of aminophosphine I7 which differ in the configuration of the phosphorus linked to t-butyl.

17

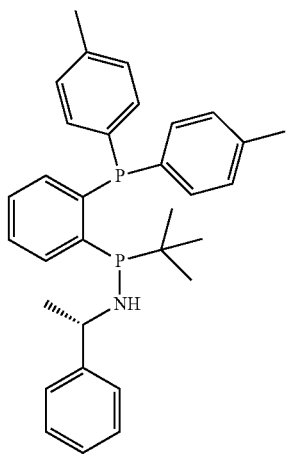

(absolute configuration not determined)

$^{31}$P NMR of the major epimer I7 ($C_6D_6$, 121 MHz): δ 38.7 (d), −11.3 (d), $J_{PP}$=160 Hz)

$^1$H NMR of the major epimer I7 ($C_6D_6$, 300 MHz), characteristic signals: δ 7.5-6.8 (several m, 17H), 3.87 (m, 1H), 2.05 (s, 3H), 2.03 (s, 3H), 1.27 (d, 3H), 1.23 and 1.19 (two s, 9H).

The major epimer I7 is used without further purification. A solution of 2.8 g (5.7 mmol) of the aminophosphine I7 in 30 ml toluene is added to 18 ml formic acid which are stirred at a temperature between 0 and 5° C. Then, cooling is removed and, after stirring for 1 hour at room temperature, the volatile parts are distilled off at 45° C. under reduced pressure. 15 ml heptane and 15 ml toluene are added to the resulting residue and the mixture is stirred for 15 minutes, whereby two phases form. The top phase is separated and the bottom phase is extracted again with the same solvent mixture. The top phases are collected and the solvents distilled off under reduced pressure giving the crude, optically enriched product B7 with an ee of 72%. Repeated recrystallization in heptane finally yields the desired product B7 with a optical purity of >99.5% ee as a colorless solid (yield 55%).

$^{31}$P NMR ($C_6D_6$, 121 MHz): δ 34.5 (d), −14.1 (d), $J_{PP}$=61 Hz)

$^1$H NMR ($C_6D_6$, 300 MHz), characteristic signals: δ 8.24 (dd, 1H, $J_{PP}$=463 Hz), 8.13 (m, 1H), 7.4-6.8 (various m, 12H), 2.02 (s, 3H), 1.99 (s, 3H), 1.17 and 1.12 (two s, 9H).

Example B8

Stereoselective Synthesis of Ligand B8

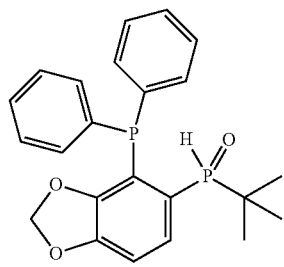

B8

To a solution of 1.24 g (3.2 mmol) of 4-bromo-3-diphenylphosphino-1,2-methylene dioxy)benzene A4 in 8 ml of THF are added dropwise, at −78° C., 2.1 ml (3.2 mmol) of n-butyllithium (1.6 M in hexane). The mixture is stirred at −78° C. for 1 hour. The reaction solution is then transferred with the aid of a cannula using elevated argon pressure into a reaction vessel in which a solution of 0.51 g (3.2 mmol) of tert-butyldichlorophosphine in 2 ml of THF is being stirred at −78° C. The cooling is removed and the mixture is stirred further at room temperature for 1.5 hour before the solvent is distilled off at 45° C. on a rotary evaporator under reduced pressure. Then 5 ml toluene and 0.7 ml ml of $NEt_3$ are added to the residue. To the resulting suspension, 0.5 ml (3.2 mmol) of (S)-(−)-alpha-methylbenzylamine are added and the mixture stirred at room temperature for several days, until formation of the aminophosphine intermediate I8 is complete. Then, the reaction mixture is extracted with water and toluene. The organic phases are collected, dried over $Na_2SO_4$ and the solvent distilled off on a rotary evaporator under reduced pressure. 1.65 g of a crude product are obtained which according to $^{31}$P-NMR consists, of an approx. 10:1 mixture of a major and a minor epimer of aminophosphine I8 which differ in the configuration of the phosphorus linked to t-butyl.

18

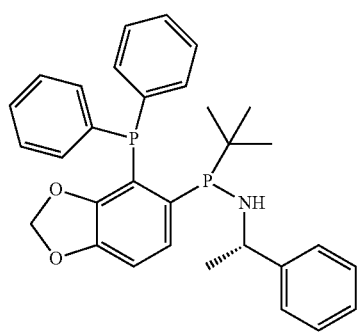

(absolute configuration not determined)

$^{31}$P NMR of the major epimer I8 ($C_6D_6$, 121 MHz): δ 39.95 (d), −19.3 (d), $J_{PP}$=174 Hz)

$^1$H NMR of the major epimer I8 (C$_6$D$_6$, 300 MHz), characteristic signals: δ 7.75-6.6 (several m, 17H), 4.96-4.93 (m, 2H), 4.07 (m, 1H), 1.42 (d, 3H), 1.18 and 1.13 (two s, 9H).

The major epimer I8 is used without further purification. A solution of 12.8 g (approx. 24 mmol) of the crude aminophosphine I8 in 50 ml toluene is added to 95 ml formic acid which are stirred at a temperature between 0 and 5° C. Then, cooling is removed and, after stirring for 1 hour at room temperature, the volatile parts are distilled off at 45° C. under reduced pressure. The residue is stirred in toluene and water and the resulting suspension is filtered. Most of the filtrate is washed down with additional toluene. The organic phases are collected, dried over Na$_2$SO$_4$, and the solvents are distilled off under reduced pressure. The residue is purified by filtration over silica gel (eluent=ethylacetate), then it is recrystallized 3 times in heptane/toluene 100:2 to give the desired product B8 as a colorless solid with a optical purity of >99.5% (50% yield).

$^{31}$P NMR (C$_6$D$_6$, 121 MHz): δ 36.0 (d), −14.1 (d), J$_{PP}$=73 Hz)

$^1$H NMR (C$_6$D$_6$, 300 MHz), characteristic signals: δ 9.15 (d, ½H), 8.20-7.45 (m, 3½H), 7.3 (m, 2H), 7.1-6.95 (m, 6H), 6.55 (d, 1H), 4.38 (s, 1H), 4.29 (s, 1H), 1.15 and 1.09 (two s, 9H).

C) PREPARATION OF METAL COMPLEXES

The Rh or Ir complexes are prepared by mixing 1 equivalent of ligand with 0.95 molar equivalent of [Rh(nbd)$_2$]BF$_4$ or [Ir(cod)$_2$]BF$_4$, in methanol or CD$_3$OD. In general, the complex is formed within less than 10 minutes. The solutions are analysed directly by means of $^{31}$P NMR. The complexes can be isolated by precipitation with, for example, heptane.

Example C1

Complex C1 ([Rh(nbd)$_2$]BF$_4$ with Ligand B2)

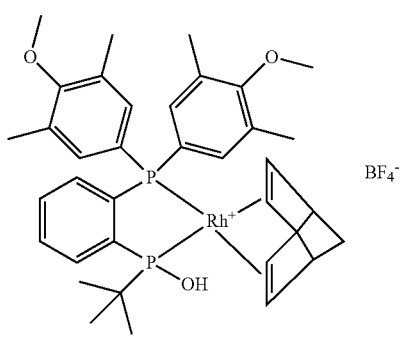

$^{31}$P NMR (CD$_3$OD, 121 MHz): δ 151.8 (dd, J=177 Hz, J=27.5 Hz), 53.8 (dd, J=165 Hz, J=27.5 Hz)

Example C2

Complex C2 ([Rh(nbd)$_2$]BF$_4$ with Ligand B4)

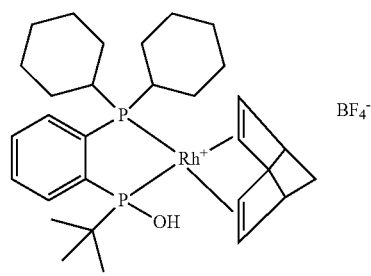

$^{31}$P NMR (CD$_3$OD, 121 MHz): δ 147.4 (dd, J=148 Hz, J=25.5 Hz), 62.2 (dd, J=161 Hz, J=25.5 Hz)

Example C3

Complex C3 ([Rh(nbd)$_2$]BF$_4$ with Ligand B6)

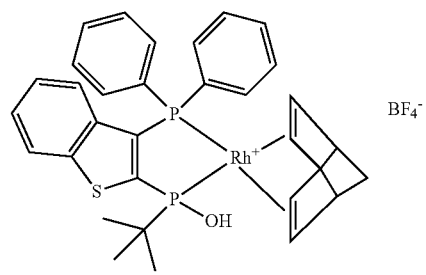

$^{31}$P NMR (CD$_3$OD, 121 MHz): δ 138.8 (dd, J=179 Hz, J=30.2 Hz), 37.8 (dd, J=162 Hz, J=30.2 Hz)

Example C4

Complex C4 ([Ir(cod)$_2$]BF$_4$ with Ligand B1)

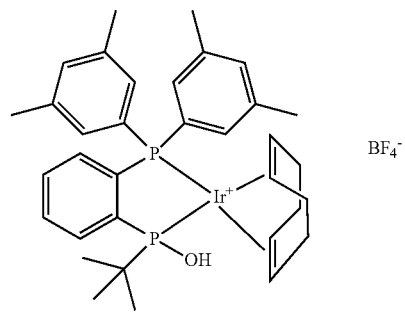

$^{31}$P NMR (CDCl$_3$, 121 MHz): δ 133.0 (d, J=3.4 Hz), 45.4 (d, J=3.4 Hz)

D) APPLICATION EXAMPLES

Examples D1-D21

Hydrogenation of Various Unsaturated Substrates

The hydrogenations are carried out in glass vials (low hydrogen pressure) or in steel autoclaves (high hydrogen pressure). Agitation is effected either by a magnetic stirrer or by shaking the reactor. The catalysts are prepared 'in situ' by mixing 1 mol-equivalent of a metal of a metal precursor (see table 2) with 1.1 mol-equivalents of ligand in the solvent given in Table 2. The substrate is dissolved in the solvent given in see table 2 and added to the catalyst as a solution. Subsequently, the inert gas is exchanged for hydrogen and the hydrogenation is started by starting agitation.

TABLE 1

| Substrate | Structures | Determination of conversion and ee |
|---|---|---|
| DMI | 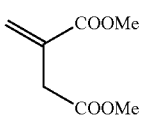 | GC with chiral column: Lipodex-E |
| MAA | 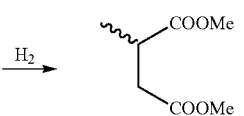 | GC with chiral column: Chirasil-L-val |
| MAC | 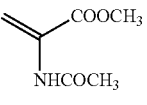 | GC with chiral column: Chirasil-L-val |
| ACA | 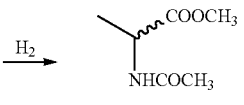 | First derivatization with TMS-diazomethane, then GC with chiral column: Chirasil-L-val |
| Z-EAAC | 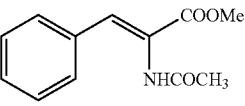 | GC with chiral column: Betadex-110 |
| E-EAAC | 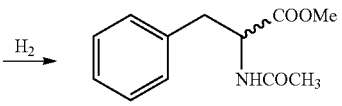 | GC with chiral column: Betadex-110 |
| MEA | 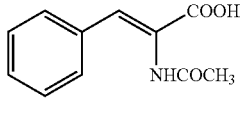 | HPLC with chiral column: Chiracel-OD-H |
| EOP | 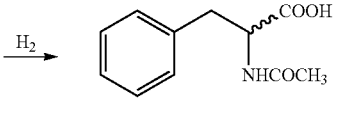 | GC with chiral column: Lipodex-E |
| EBA | 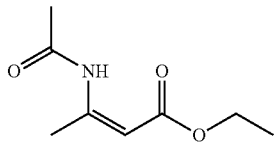 | HPLC with chiral column: Chiracel-OD-H |

TABLE 1-continued

| Substrate | Structures | Determination of conversion and ee |
|---|---|---|
| ETAA | 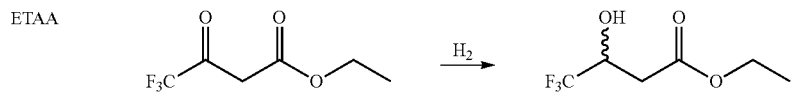 | GC with chiral column: Lipodex-E |

The abbreviations in Table 2 mean:

ee = enantiomeric excess,

GC = gas chromatography,

TMS = trimethylsilyl,

HPLC = high-pressure liquid chromatography.

TABLE 2

Hydrogenation results

| No. | Lig. | Metal | Substrate | [S] | S/C | Solvent | P | T | t [h] | C (%) | ee (%) |
|---|---|---|---|---|---|---|---|---|---|---|---|
| D1 | A | Rh[a] | MAA | 0.25 | 200 | MeOH | 1 | 25 | 1 | 100 | 99.8 |
| D2 | A | Rh[a] | MAC | 0.25 | 200 | MeOH | 1 | 25 | 1 | 100 | 96.1 |
| D3 | A | Rh[a] | DMI | 0.25 | 200 | MeOH | 1 | 25 | 1 | 100 | 99.9 |
| D4 | B1 | Rh[a] | MAA | 0.25 | 200 | MeOH | 1 | 25 | 1 | 100 | 99.9 |
| D5 | B2 | Rh[a] | MAA | 0.25 | 200 | MeOH | 1 | 25 | 0.1 | 100 | 99.9 |
| D6 | B2 | Rh[a] | MAC | 0.25 | 200 | MeOH | 1 | 25 | 1 | 100 | 97.9 |
| D7 | B5 | Rh[a] | MAA | 0.25 | 200 | MeOH | 1 | 25 | 1 | 100 | 94.2 |
| D8 | B6 | Rh[a] | MAA | 0.25 | 200 | MeOH | 1 | 25 | 1 | 100 | 99.9 |
| D9[1] | A | Ru[b] | EOP | 0.5 | 1000 | EtOH | 80 | 80 | 18 | 63 | 83.2 |
| D10[2] | B7 | Rh[a] | ACA | 0.36 | 100 | EtOH | 1 | 25 | 2 | 100 | >99.9 |
| D11 | B7 | Rh[a] | DMI | 0.36 | 100 | THF | 1 | 25 | 2 | 100 | >99.9 |
| D12 | B7 | Rh[a] | E-EAAC | 0.36 | 100 | EtOH | 1 | 25 | 2 | 100 | >99.9 |
| D13 | B7 | Rh[a] | Z-EAAC | 0.36 | 100 | EtOH(9) TFE(1) | 1 | 25 | 2 | 100 | 83.8 |
| D14 | B7 | Rh[a] | MAC | 0.36 | 100 | EtOH | 1 | 25 | 2 | 100 | 99.7 |
| D15 | B7 | Rh[a] | MAA | 0.36 | 100 | EtOH | 1 | 25 | 2 | 100 | >99.9 |
| D16 | B7 | Rh[a] | DMI | 0.25 | 200 | MeOH | 1 | 25 | 0.02 | 100 | 98.3 |
| D17 | B7 | Ir[c] | EOP | 0.1 | 25 | EtOH | 80 | 80 | 14 | 63 | 89.8 |
| D18 | B7 | Rh[a] | ETAA | 0.36 | 100 | THF | 80 | 80 | 14 | 100 | 51.5 |
| D19[3] | B7 | Ru[e] | ETAA | 0.36 | 100 | EtOH | 80 | 80 | 14 | 100 | 54.4 |
| D20 | B7 | Ir[c] | EBA | 0.1 | 25 | DCE | 80 | 80 | 14 | 100 | 84.5 |
| D21 | B7 | Ru[b] | EBA | 0.1 | 25 | EtOH | 80 | 80 | 14 | 85 | 79.5 |
| D22 | B8 | Rh[a] | MAA | 0.25 | 200 | MeOH | 1 | 25 | 1 | 100 | 99.7 |
| D23 | B8 | Rh[a] | DMI | 0.25 | 200 | MeOH | 1 | 25 | 1 | 100 | 98.4 |

Additions:

[1] 1N HCl (0.6% based on solvent volume);

[2] 12 mol-equivalents of 1,4-diazobicyclo[2.2.2]octane/metal;

[3] 2.5 mol-equivalents of acetylchloride/metal.

In the table 2:

[S] means molar substrate concentration;

S/C means substrate/catalyst ratio;

t means hydrogenation time;

Lig. means ligand,

Sol. means solvent (MeOH = methanol; EtOH = ethanol; Tol = toluene; THF = tetrahydrofuran; DCE = 1,2-dichloroethane, TFE = 2,2,2-Trifluoroethanol);

Metal means metal precursor which is used in the hydrogenations:

Rh[a] = [Rh(norbornadiene)$_2$]BF$_4$;

Ru[b] = [RuI$_2$(p-methylcumene)]$_2$;

[Ir[c]] = [Ir(cyclooctadiene)Cl]$_2$;

Lig. = ligand,

C = conversion;

Conf. = configuration.

The invention claimed is:

1. A compound of the formula (I), in the form of a mixture comprising predominantly one enantiomer, or in the form of a pure enantiomer,

 (I)

wherein secondary phosphine corresponds to the formula —PR$_2$R$_3$, wherein R$_2$ and R$_3$ are each independently a hydrocarbon radical or an O-atom(s) containing heterohydrocarbon radical which has 1 to 18 carbon atoms and is unsubstituted or substituted by C$_1$-C$_6$-alkyl, trifluoro-methyl, C$_1$-C$_6$-alkoxy, trifluoromethoxy, (C$_1$-C$_4$-alkyl)$_2$amino, (C$_6$H$_5$)$_3$Si, (C$_1$-C$_{12}$-alkyl)$_3$Si, or halogen;

Q is a substituted or unsubstituted radical of the formulae:

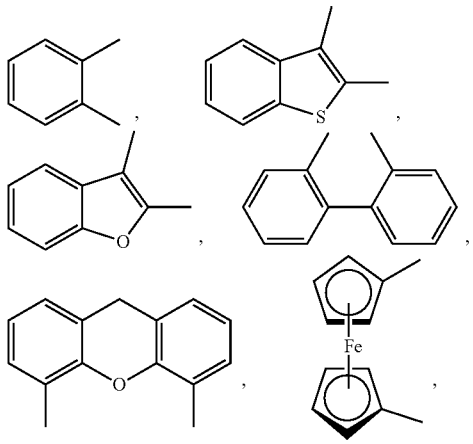

or linear C$_1$-C$_4$-alkylene, wherein the secondary phosphine group is bonded directly to a carbon atom in Q, and wherein —P*(=O)HR$_1$ is bonded directly to a carbon atom in Q;

P* is a chiral phosphorus atom; and

R$_1$ is a hydrocarbon radical selected from the group consisting of linear or branched C$_1$-C$_{18}$-alkyl-; unsubstituted or C$_1$-C$_6$-alkyl- or C$_1$-C$_6$-alkoxy-substituted C$_5$-C$_{12}$-cycloalkyl- or C$_5$-C$_{12}$-cycloalkyl-CH$_2$—; phenyl, naphthyl, anthryl or benzyl; or halogen-, C$_1$-C$_6$-alkyl-, trifluoromethyl-, C$_1$-C$_6$-alkoxy-, trifluoromethoxy-, (C$_6$H$_5$)$_3$Si—, (C$_1$-C$_{12}$-alkyl)$_3$Si—, and secondary amino-substituted phenyl, naphthyl or benzyl;

excluding the compound of the formula A

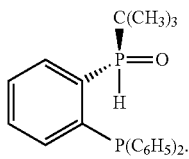 (A)

2. A compound according to claim 1, wherein Q is an unsubstituted or substituted radical of the formulae

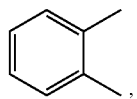

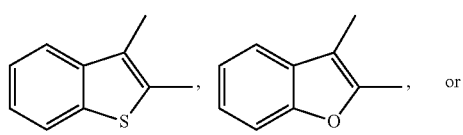

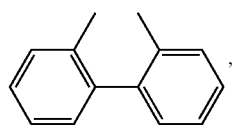

R$_1$ is linear or branched C$_1$-C$_8$-alkyl, cyclopentyl or cyclohexyl which are unsubstituted or substituted by 1 to 3 C$_1$-C$_4$-alkyl or C$_1$-C$_4$-alkoxy; benzyl, phenyl, naphtyl or anthryl which are unsubstituted or substituted by 1 to 3 C$_1$-C$_4$-alkyl, C$_1$-C$_4$-alkoxy, C$_1$-C$_4$-fluoroalkyl, F or Cl.

3. A compound according to claim 1, wherein Q is unsubstituted

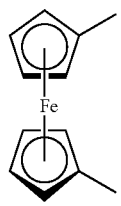

the —PR$_2$R$_3$ group is linked to Q directly or via —CH$_2$—, —(CH$_2$)—or C$_2$-C$_6$-alkylidene; and R$_1$ is C$_1$-C$_8$-alkyl, cyclopentyl or cyclohexyl which are unsubstituted or substituted by 1 to 3 C$_1$-C$_4$-alkyl or C$_1$-C$_4$-alkoxy; benzyl, phenyl, naphtyl or anthryl which are unsubstituted.

4. A compound according to claim 1, wherein Q is unsubstituted or C$_1$-C$_4$-alkyl-substituted C$_1$-C$_4$-alkylene.

5. A compound according to claim 1, wherein Q is unsubstituted or C$_1$-C$_4$-alkyl-substituted C$_1$-C$_4$-alkylene;

R$_1$ is C$_1$-C$_8$-alkyl, cyclopentyl or cyclohexyl which are unsubstituted or substituted by 1 to 3 C$_1$-C$_4$-alkyl or C$_1$-C$_4$-alkoxy; benzyl, phenyl, naphtyl or anthryl which are unsubstituted or substituted by 1 to 3 C$_1$-C$_4$-alkyl, C$_1$-C$_4$-alkoxy, C$_1$-C$_4$-fluoroalkyl, F or Cl.

6. A compound according to claim 1, selected from the group consisting of:

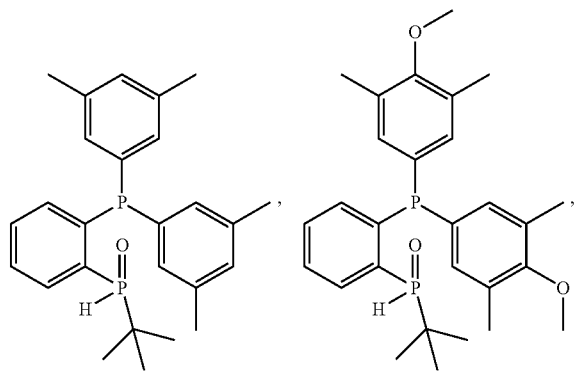

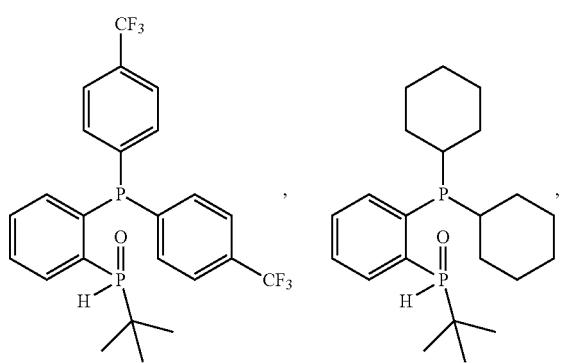

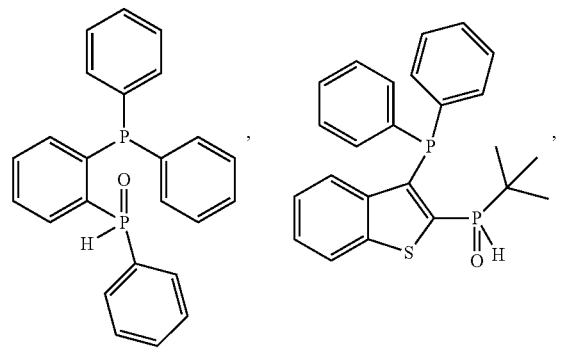

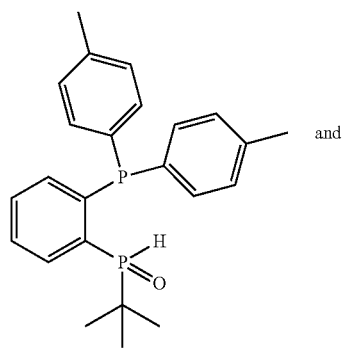 and

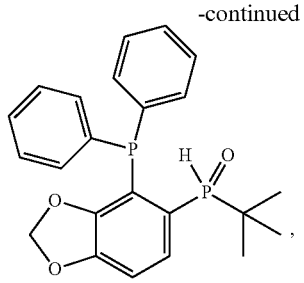

wherein the absolute configuration on the stereogenic P is R or S.

7. A process for preparing a compound of formula (I) of claim 1, comprising:

reacting a compound of the formula (II), secondary phosphine-Q-Hal (II), wherein the secondary phosphine is a group of the formula —PR$_2$R$_3$, wherein R$_2$ and R$_3$ are each as defined in formula (I) of claim 1, Q is as defined in formula (I) of claim 1, and Hal is Cl, Br or I, with a metallating reagent to obtain an intermediate, and then reacting the intermediate with a halophosphine of the formula (III), R$_1$—P(Hal$_1$)$_2$ (III), wherein:
R$_1$ is as defined in formula (I) of claim 1, and
Hal$_1$ is Cl, Br or I,
to form a compound of the formula (IV), secondary phosphine-Q-P Hal$_1$R$_1$ (IV), wherein secondary phosphine, Q, Hal$_1$ and R$_1$ are as defined above, and then hydrolyzing the compound of formula (IV) with water to obtain a racemic compound of the formula (I), and then optically resolving the racemic compound of the formula (I) to obtain the compound of the formula (I) of claim 1.

8. A process for preparing a compound of formula (I) of claim 1, comprising:

reacting a compound of the formula (II), secondary phosphine-Q-Hal (II), wherein the secondary phosphine is a group of the formula —PR$_2$R$_3$, wherein R$_2$ and R$_3$ are each as defined in formula (I) of claim 1, Q is as defined in formula (I) of claim 1 and Hal is Cl, Br or I, with a metallating reagent to obtain an intermediate, and then reacting the intermediate with a halophosphine of the formula (III), R$_1$—P(Hal$_1$)$_2$ (III), wherein:
R$_1$ is as defined in formula (I) of claim 1, and
Hal$_1$ is Cl, Br or I,
to obtain a compound of the formula (IV), secondary phosphine-Q-P Hal$_1$R$_1$ (IV), wherein secondary phosphine, Q, Hal$_1$ and R$_1$ are as defined above, and then reacting the compound of formula (IV) with a chiral, optically pure or enriched primary amine, secondary amine or alcohol of the formula H—X*, wherein H is hydrogen and X* is an optically enriched or optically pure chiral group of the formula G-C*R'R"R'",
wherein:
C* is an asymmetric carbon atom,
G is O, HN or (R"")N, wherein R"" is $C_1$-$C_8$-alkyl, $C_5$-$C_8$-cycloalkyl, $C_6$-$C_{10}$-aryl, $C_7$-$C_{12}$-aralkyl, or $C_7$-$C_{12}$-alkaralkyl, and
R', R", and R'" are different and are independently a hydrogen radical, a hydrocarbon radical or a heterohydrocarbon radical,
to obtain a diastereomerically enriched compound of the formula (IV*)

secondary phosphine-Q-PX*$R_1$ (IV*), and then hydrolyzing or treating the compound of formula (IV*) with a neat acid to obtain the compound of formula (I) of claim 1.

9. A metal complex of a transition metal with a compound of claim 1, wherein the transition metal is selected from the group consisting of the transition groups of the Periodic Table of the Elements.

10. A process for preparing a chiral organic compound comprising:
asymmetric addition of hydrogen onto a carbon or carbon-heteroatom double bond in a prochiral organic compound in the presence of a catalyst,
wherein the addition is carried out in the presence of a catalytic amount of at least one metal complex according to claim 9,
with the proviso that the prochiral organic compound is not 1-phenylvinyl dimethyl-carbamate or N-benzyl-N-[1-phenylethylidene]amine.

11. A method for preparing a chiral organic compound comprising:
asymmetric addition of hydrogen onto a carbon or carbon-heteroatom double bond in a prochiral organic compound, and
employing a metal complex of a transition metal with a compound of claim 1 as a homogeneous catalyst, wherein the transition metal is selected from the group consisting of the transition groups of the Periodic Table of the Elements.

12. A compound according to claim 4, wherein Q is unsubstituted methylene or ethylene.

13. A process for preparing a compound of formula (I) of claim 1, comprising:

reacting a compound of the formula (II'), secondary phosphine-Q-active hydrogen (II'), wherein the secondary phosphine is a group of the formula —$PR_2R_3$, wherein $R_2$ and $R_3$ are each as defined in formula (I) of claim 1 and Q is as defined in formula (I) of claim 1, with a metallating reagent to obtain an intermediate, and
then reacting the intermediate with a halophosphine of the formula (III), $R_1$—P($Hal_1$)$_2$ (III), wherein:
$R_1$ is as defined in formula (I) of claim 1, and
$Hal_1$ is Cl, Br or I,
to form a compound of the formula (IV), secondary phosphine-Q-P $Hal_1R_1$ (IV), wherein secondary phosphine, Q, $Hal_1$ and $R_1$ are as defined above, and then hydrolyzing the compound of formula (IV) with water to obtain a racemic compound of the formula (I), and
then optically resolving the racemic compound of the formula (I) to obtain the compound of the formula (I) of claim 1.

14. The process according to claim 8, wherein R"" is a cyclohexyl, phenyl, benzyl, or methylbenzyl.

15. A process for preparing a compound of formula (I) of claim 1, comprising:

reacting a compound of the formula (II'), secondary phosphine-Q-active hydrogen (II'), wherein the secondary phosphine is a group of the formula —$PR_2R_3$, wherein $R_2$ and $R_3$ are each as defined in formula (I) of claim 1, and Q is as defined in formula (I) of claim 1, with a metallating reagent to obtain an intermediate, and
then reacting the intermediate with a halophosphine of the formula (III), $R_1$—P($Hal_1$)$_2$ (III), wherein:
$R_1$ is as defined in formula (I) of claim 1, and
$Hal_1$ is Cl, Br or I,
to obtain a compound of the formula (IV), secondary phosphine-Q-P $Hal_1R_1$ (IV), wherein secondary phosphine, Q, $Hal_1$ and $R_1$ are as defined above, and then reacting the compound of formula (IV) with a chiral, optically pure or enriched primary amine, secondary amine or alcohol of the formula H—X*,
wherein H is hydrogen and X* is an optically enriched or optically pure chiral group of the formula G-C*R'R"R'",
wherein:
C* is an asymmetric carbon atom,
G is O, HN or (R"")N, wherein R"" is $C_1$-$C_8$-alkyl, $C_5$-$C_8$-cycloalkyl, $C_6$-$C_{10}$-aryl, $C_7$-$C_{12}$-aralkyl, or $C_7$-$C_{12}$-alkaralkyl, and
R', R", and R'" are different and are independently a hydrogen radical, a hydrocarbon radical or
a heterohydrocarbon radical,
to obtain a diastereomerically enriched compound of the formula (IV*)

secondary phosphine-Q-PX*$R_1$ (IV*), and then hydrolyzing or treating the compound of formula (IV*) with a neat acid to obtain the compound of formula (I) of claim 1.

16. The process according to claim 15, wherein R"" is a cyclohexyl, phenyl, benzyl, or methylbenzyl.

* * * * *

UNITED STATES PATENT AND TRADEMARK OFFICE
CERTIFICATE OF CORRECTION

PATENT NO.       : 8,415,488 B2                                    Page 1 of 1
APPLICATION NO.  : 12/734726
DATED            : April 9, 2013
INVENTOR(S)      : Benoit Pugin et al.

It is certified that error appears in the above-identified patent and that said Letters Patent is hereby corrected as shown below:

In the Claims

Claim 7, in column 40, line 22:
"–$PR_2R_1R_3$, wherein $R_2$ and $R_3$ are each as defined in", should read
-- –$PR_2R_3$, wherein $R_2$ and $R_3$ are each as defined in --.

Claim 8, in column 41, line 5:
"G is O, HN or (R''''')N, wherein R'''' is $C_1$-$C_8$-alkyl, $C_5$-$C_8$-", should read
-- G is O, HN or (R'''')N, wherein R'''' is $C_1$-$C_8$-alkyl, $C_5$-$C_8$- --.

Claim 8, in column 41, line 6:
"cycloalky, $C_6$-$C_{10}$-aryl, $C_7$ $C_{12}$-aralkyl, or $C_7$-$C_{12}$-", should read
-- cycloalky, $C_6$-$C_{10}$-aryl, $C_7$-$C_{12}$-aralkyl, or $C_7$-$C_{12}$- --.

Claim 15, in column 42, line 45:
"G is O, HN or (R'''')N, wherein R''' is $C_1$-$C_8$-alkyl, $C_5$-$C_8$-", should read
-- G is O, HN or (R'''')N, wherein R'''' is $C_1$-$C_8$-alkyl, $C_5$-$C_8$- --.

Signed and Sealed this
Thirtieth Day of July, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,415,488 B2  
APPLICATION NO. : 12/734726  
DATED : April 9, 2013  
INVENTOR(S) : Benoit Pugin et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 263 days.

Signed and Sealed this  
Tenth Day of December, 2013

Margaret A. Focarino  
*Commissioner for Patents of the United States Patent and Trademark Office*